US008932797B2

(12) United States Patent
Thackeray et al.

(10) Patent No.: US 8,932,797 B2
(45) Date of Patent: Jan. 13, 2015

(54) PHOTOACID GENERATORS

(75) Inventors: James W. Thackeray, Braintree, MA (US); Suzanne M. Coley, Mansfield, MA (US); James F. Cameron, Brookline, MA (US); Paul J. LaBeaume, Framingham, MA (US); Ahmad E. Madkour, Midland, MI (US); Owendi Ongayi, Marlborough, MA (US); Vipul Jain, Westborough, MA (US)

(73) Assignees: Dow Global Technologies LLC, Midland, MI (US); Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 13/307,198

(22) Filed: Nov. 30, 2011

(65) Prior Publication Data
US 2012/0141939 A1 Jun. 7, 2012

Related U.S. Application Data

(60) Provisional application No. 61/418,196, filed on Nov. 30, 2010.

(51) Int. Cl.
G03F 7/004 (2006.01)
C07C 303/32 (2006.01)
C07C 309/04 (2006.01)
C07C 309/06 (2006.01)
C07C 309/12 (2006.01)
C07C 309/29 (2006.01)
C07C 309/30 (2006.01)
C07C 309/39 (2006.01)
C07C 381/12 (2006.01)
G03F 7/039 (2006.01)

(52) U.S. Cl.
CPC ............ *C07C 381/12* (2013.01); *G03F 7/0045* (2013.01); *G03F 7/0046* (2013.01); *G03F 7/0397* (2013.01); *Y10S 430/111* (2013.01); *Y10S 430/121* (2013.01); *Y10S 430/122* (2013.01); *Y10S 430/123* (2013.01)
USPC ...................... 430/270.1; 430/271.1; 430/326; 430/910; 430/920; 430/921; 430/922; 562/37; 562/100; 562/109; 562/113; 568/74; 568/77

(58) Field of Classification Search
CPC ... G03F 7/0045; G03F 7/0397; C07C 381/12; C07C 303/32; C07C 309/04; C07C 309/06; C07C 309/12; C07C 309/29; C07C 309/30; C07C 309/39; C07C 382/12
USPC ........... 430/270.1, 921, 922, 271.1, 326, 910, 430/920; 562/37, 100, 109, 113; 568/74, 77
See application file for complete search history.

(56) References Cited

U.S. PATENT DOCUMENTS

| 4,451,409 | A | 5/1984 | Buske et al. |
|---|---|---|---|
| 5,824,824 | A | 10/1998 | Osawa et al. |
| 6,060,207 | A | 5/2000 | Shida et al. |
| 6,111,143 | A * | 8/2000 | Park et al. ............ 568/35 |
| 6,458,506 | B2 | 10/2002 | Cameron |
| 6,548,221 | B2 | 4/2003 | Uetani et al. |
| 6,664,022 | B1 | 12/2003 | Cameron et al. |
| 7,682,772 | B2 * | 3/2010 | Seshimo et al. ......... 430/270.1 |
| 7,776,510 | B2 | 8/2010 | Iwai et al. |
| 2002/0001770 | A1 | 1/2002 | Cameron |
| 2003/0013049 | A1 | 1/2003 | Cameron et al. |
| 2004/0137369 | A1* | 7/2004 | Shimada ................. 430/281.1 |
| 2004/0241569 | A1* | 12/2004 | Chen et al. ............... 430/176 |
| 2004/0265733 | A1 | 12/2004 | Houlihan et al. |
| 2006/0216635 | A1 | 9/2006 | Hirano et al. |
| 2007/0149702 | A1* | 6/2007 | Ando et al. ............... 524/556 |
| 2007/0224540 | A1 | 9/2007 | Kamimura et al. |
| 2007/0298352 | A1 | 12/2007 | Kobayashi et al. |

(Continued)

FOREIGN PATENT DOCUMENTS

EP 0834770 A2 4/1998
EP 1030221 A1 8/2000

(Continued)

OTHER PUBLICATIONS

JP2008127300A; Jun. 5, 2008; Abstract Only (1 page).

(Continued)

*Primary Examiner* — John Chu
(74) *Attorney, Agent, or Firm* — Cantor Colburn LLP

(57) ABSTRACT

A photoacid generator compound has formula (I):

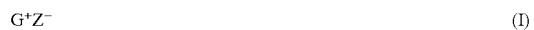

$$G^+Z^- \quad (I)$$

wherein G has formula (II):

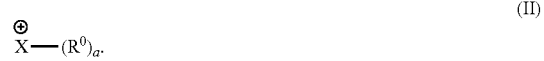

In formula (II), X is S or I, each $R^0$ is commonly attached to X and is independently $C_{1-30}$ alkyl; polycyclic or monocyclic $C_{3-30}$ cycloalkyl; polycyclic or monocyclic $C_{6-30}$ aryl; or a combination comprising at least one of the foregoing groups. G has a molecular weight greater than 263.4 g/mol, or less than 263.4 g/mol. One or more $R^0$ groups are further attached to an adjacent $R^0$ group, a is 2 or 3, wherein when X is I, a is 2, or when X is S, a is 2 or 3. Z in formula (I) comprises the anion of a sulfonic acid, a sulfonimide, or a sulfonamide. A photoresist and coated film also includes the photoacid generator, and a method of forming an electronic device uses the photoresist.

18 Claims, No Drawings

(56) References Cited

U.S. PATENT DOCUMENTS

| | | |
|---|---|---|
| 2008/0076063 A1 | 3/2008 | Yoshida et al. |
| 2008/0085468 A1* | 4/2008 | Kamimura et al. ........ 430/286.1 |
| 2009/0246683 A1 | 10/2009 | Watanabe et al. |

FOREIGN PATENT DOCUMENTS

| | | |
|---|---|---|
| EP | 1705518 A2 | 9/2006 |
| EP | 1906241 A1 | 4/2008 |
| EP | 2020616 A2 | 2/2009 |
| EP | 2332960 A2 | 6/2011 |
| WO | 0219033 A2 | 3/2002 |
| WO | 03072567 A1 | 9/2003 |

OTHER PUBLICATIONS

JP2008169231A; Jul. 24, 2008; Abstract Only (1 page).

JP2010044253A; Feb. 25, 2010; Abstract Only (1 page).

WO2010123101A1; Oct. 28, 2010; Abstract Only (1 page).

JP2006276760; Oct. 12, 2006; Fuji Photo Film Co Ltd; English Translation; 68 pages.

JP2009069381; Apr. 2, 2009; Fujifilm Corp; English Translation; 104 pages.

G.H. Ho et al., "Ionic Outgassing from Photoacid Generators Upon Irradiation at 13.5 nm", Microelectronic Engineering; 2008, pp. 2213-2219, vol. 85.

H. Oizumi et al., "Development of New Negative-Tone Molecular Resits Based on Calixarene for EUV Lithography", Journal of Photopolymer Science and Technology; 2008, pp. 443-449, vol. 21, No. 3.

I. Pollentier, "Study of EUV Resist Outgassing/Contamination for Device Integration using EUVL Processes", Journal of Photopolymer Science and Technology; 2010, pp. 605-612, vol. 23, No. 5.

S. Kobayashi et al., "Analysis of Outgassing from EUV Resists", Journal of Photopolymer Science and Technology; 2007, pp. 445-451, vol. 20, No. 3.

S. Kobayashi et al., "EUV Resist Outgassing: Quantification and Release Mechanisms", Journal of Photopolymer Science and Technology; 2008, pp. 469-474, vol. 21, No. 4.

S. Masuda et al., "Reduction of the Outgassing Segment in Acetal Based Chemically Amplified Resist for EUV Lithography", Journal of Photoploymer Science and Technology; 2006, pp. 533-538, vol. 19, No. 4.

T. Watanabe et al., "Mitigation of Low Outgassing and Small Line Edge Roughness for EUVL Resist", Journal of Photopolymer Science and Technology; 2004, pp. 361-366, vol. 17, No. 3.

JP2009280535 A, Dec. 3, 2009, Abstract Only, 1 page.

\* cited by examiner

PHOTOACID GENERATORS

CROSS-REFERENCE TO RELATED APPLICATION

This application is a nonprovisional of U.S. Provisional Application No. 61/418,196, filed on Nov. 30, 2010, the content of which is incorporated by reference herein in its entirety.

BACKGROUND

Chemical compounds which decompose to generate acids when exposed to radiation (referred to herein as "photoacid generators") in the ultraviolet region of the spectrum (i.e., <300 nm) are the basis for "chemically amplified" deprotection or crosslinking of polymers in chemically amplified photoresists for microelectronics applications. The decomposition products of such photoresists including primarily low molecular weight organic molecules such as isobutylene (from high activation energy photoresists) and acetaldehyde (from low activation energy photoresists), but also decomposition products from the photoacid generator, have been observed in photoresists used in imaging tools (steppers) operating at wavelengths of, for example, 248 nm and 193 nm. Outgassing of such materials can coat and corrode the optics.

Measures have been implemented to limit the effects of outgassing of decomposition products such as, for example, cleaning the optics and/or including sacrificial barriers or filters between the optics and the photoresist coating. However, with the industry trend toward increased resolution at smaller and smaller linewidths of less than 45 nm, and with the development of new tools operating at significantly shorter wavelengths (such as in the extreme ultraviolet (EUV) region at 13.5 nm) and having advanced reflective optics, there is renewed interest in control of outgas sing at the compositional level in a photoresist.

Photoresists have been studied for their contribution to the outgas sing of photoresists during EUV exposure. Pollentier ("Study of EUV Resist Outgassing/Contamination for Device Integration using EUVL Processes," Pollentier, I., *J. Photopolym. Sci. Technol.*, 2010, vol. 23(5), pp. 605-612) has found, after testing several photoresists for outgassing by residual gas analysis (RGA) in which a sample is exposed in a sealed chamber, and the atmosphere after exposure is analyzed by gas chromatography/mass spectrometry, that several of the primary decomposition products of the photoresists tested include low molecular weight compounds such as benzene and diphenyl sulfide, attributed to decomposition products of the photoacid generator (for example, where the photoacid generator studied was triphenylsulfonium trifluoromethane sulfonate). In particular, volatile decomposition products that include sulfur are of concern as these materials may not be effectively cleaned from the optics, which is further problematic as ionic photoacid generators based on the triphenylsulfonium cation have desirably high sensitivity and provide fast photospeed (<10 mJ/cm$^2$) in photoresists.

STATEMENT OF INVENTION

The above and other deficiencies of the prior art may be overcome by, in an embodiment, a photoacid generator compound of the formula (I):

$$G^+Z^- \quad (I)$$

wherein G has the formula (II):

wherein in formula (II), X is S or I, each R$^0$ is commonly attached to X and is independently a C$_{1-30}$ alkyl group; a polycyclic or monocyclic C$_{3-30}$ cycloalkyl group; a polycyclic or monocyclic C$_{6-30}$ aryl group; or a combination comprising at least one of the foregoing, G has a molecular weight of greater than 263.4 g/mol, or G has a molecular weight of less than 263.4 g/mol and one or more R$^0$ groups are further attached to an adjacent R$^0$ group, a is 2 or 3, wherein when X is I, a is 2, or when X is S, a is 3, and Z in formula (I) comprises the anion of a sulfonic acid, a sulfonimide, or a sulfonamide.

In another embodiment, a photoresist comprises the photoacid generator compound and a polymer comprising acid sensitive functional groups.

In another embodiment, a coated substrate comprises (a) a substrate having one or more layers to be patterned on a surface thereof; and (b) a layer of a photoresist composition over the one or more layers to be patterned.

In another embodiment, a method of forming an electronic device comprises (a)applying a layer of a photoresist composition of claim 9 on a substrate; (b) patternwise exposing the photoresist composition layer to activating radiation; and (c) developing the exposed photoresist composition layer to provide a resist relief image.

DETAILED DESCRIPTION

Disclosed herein are novel photoacid generators (herein, PAGs) having low outgassing properties when exposed to actinic radiation, and in particular, when used in photoresist compositions exposed to radiation for advanced lithographies, such as for e-beam, x-ray, and extreme ultraviolet (EUV) radiation having a wavelength of 13.5 nm. The photoacid generators are salts of onium cations which have high sensitivity to these actinic radiations, but where the decomposition products of these PAGs are reduced relative to conventional PAGs having, for example, diphenyliodonium cations and triphenylsulfonium cations, under similar conditions of photoresist composition, exposure, and processing.

As used herein "onium" refers to iodonium or sulfonium cations. Also as used herein, "substituted" means including a substituent such as a halogen (i.e., F, Cl, Br, I), hydroxy, amino, thiol, carboxyl, carboxylate, amide, nitrile, thiol, sulfide, disulfide, nitro, a C$_{1-10}$ alkyl, a C$_{1-10}$ alkoxy, a C$_{6-10}$ aryl, a C$_{6-10}$ aryloxy, a C$_{7-10}$ alkyl aryl, a C$_{7-10}$ alkyl aryloxy, or a combination comprising at least one of the foregoing. It will be understood that any group or structure disclosed with respect to the formulas herein may be so substituted unless otherwise specified, or where such substitution would significantly adversely affect the desired properties of the resulting structure. Also, "(meth)acrylate as used herein means either acrylate or methacrylate, and is not limited to either of these unless otherwise specified.

The PAGs disclosed herein are based on a cation-anion structure in which the cation is an aryl-substituted onium (i.e., disubstituted iodonium or trisubstituted sulfonium) cation, either of a molecular weight greater than that of a triphenyl sulfonium cation, or of a structure in which the substituent aryl groups are further attached to one or more adjacent aryl groups in, for example, a heterocycle structure which includes the onium, or as part of a fused aromatic ring system.

The PAG disclosed herein thus include a compound having the formula (I):

$$G^+Z^- \quad (I)$$

wherein G is the aryl-substituted onium cation, and Z is an anion based on the conjugate base of a suitable strong acid (e.g., a sulfonic acid or the anion of a sulfonimide).

G has the formula (II):

(II)

wherein in formula (II), X is an onium heteroatom and is preferably S or I. Each $R^0$ is commonly attached to X and is independently a $C_{1-30}$ alkyl group; a polycyclic or monocyclic $C_{3-30}$ cycloalkyl group; a polycyclic or monocyclic $C_{6-30}$ aryl group; or a combination comprising at least one of the foregoing.

The cation G (as represented by formula (II)) may have a molecular weight of greater than 263.4 g/mol (i.e., greater than that of the triphenylsulfonium cation $(C_6H_5)_3S^+$, also referred to herein as TPS cation). Where G has a greater molecular weight than the TPS cation, it will be understood that the aryl substituent groups are further structurally larger than TPS, and that the decomposition products of G are therefore greater in molecular weight than the corresponding decomposition products of TPS.

Alternatively, G in formula (II) may have a molecular weight of less than 263.4 g/mol, provided one or more $R^0$ groups are further attached to an adjacent $R^0$ group. For example, adjacent phenyl groups commonly attached to the onium heteroatom (I or S) center may be further attached to each other ortho to the point of attachment between the phenyl group and the onium heteroatom (or meta, or para, or independently through different points of attachment as where one aryl is a phenyl, and the adjacent aryl is different, e.g., a naphthyl, anthracyl, etc.), by a single bond or by a $C_{1-20}$ bridging group such as a methylene or substituted methylene, a heteroatom such as O, S, N, or the like, or a longer bridge such as an ethylene, trimethylene, o- or m-phenylene, etc. In this way in this example, an ortho-disubstituted biphenyl fused five membered ring is obtained, where the biphenyl is commonly connected to the onium heteroatom.

Also in formula (II), a is 2 or 3, wherein when X is I, a is 2, or when X is S, a is 3. It will be further appreciated that as discussed above, the number of $R^0$ groups may refer to either independent $R^0$ groups, or may refer to one-half of an $R^0$ group attached to X where two $R^0$ groups are attached in common with each other and with X, or to one-third of a group attached to X where three $R^0$ groups are attached to each other and to X.

Preferred PAG compounds includes where G is of the formula (III), (IV), or (V):

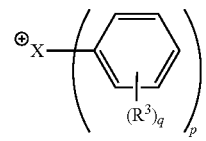
(III)

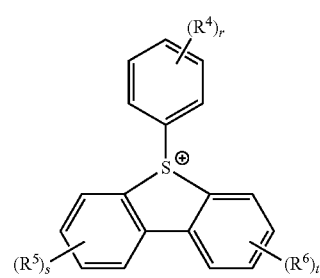
(IV)

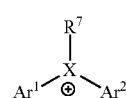
(V)

wherein X is I or S, each $R^3$, $R^4$, $R^5$, and $R^6$ is independently a single bond to an adjacent phenyl group, hydroxy, nitrile, halogen, $C_{1-10}$ alkyl, $C_{1-10}$ fluoroalkyl, $C_{1-10}$ alkoxy, $C_{1-10}$ fluoroalkoxy, $C_{6-20}$ aryl, $C_{6-20}$ fluoroaryl, $C_{6-20}$ aryloxy, $C_{6-20}$ fluoroaryloxy, $C_{1-20}$ alkylene, or $C_{1-20}$ alkoxylene group; p is 2 or 3, wherein when X is I, p is 2, and where X is S, p is 2 or 3; and each q and r is independently an integer from 0 to 5, and s and t are independently an integer from 0 to 4. It will be further appreciated that in formula (III), where X is S and p is 2, at least one $R^2$ is an $C_{1-20}$ alkylene or $C_{1-20}$ alkoxylene group connecting an aryl group to X. In formula (V), $Ar^1$ and $Ar^2$ are further independently $C_{10-30}$ fused or singly bonded polycyclic aryl groups including structures based on naphthyl, biphenyl, anthracenyl, phenanthrenyl, bis-aryl ether, and combinations including these structures (e.g., phenyl-naphthyl, biphenyl-naphthyl, etc.); and $R^7$ is a lone pair of electrons (where X is I), or a $C_{6-20}$ aryl group (where X is S) and may further include substituents such as those generally disclosed hereinabove.

Exemplary PAG cations G in formula (I) include the following structures:

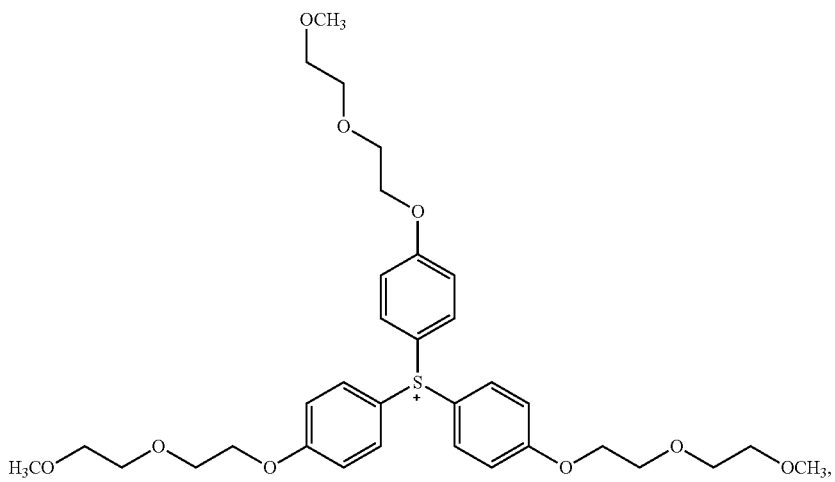

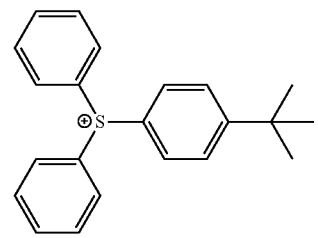

,

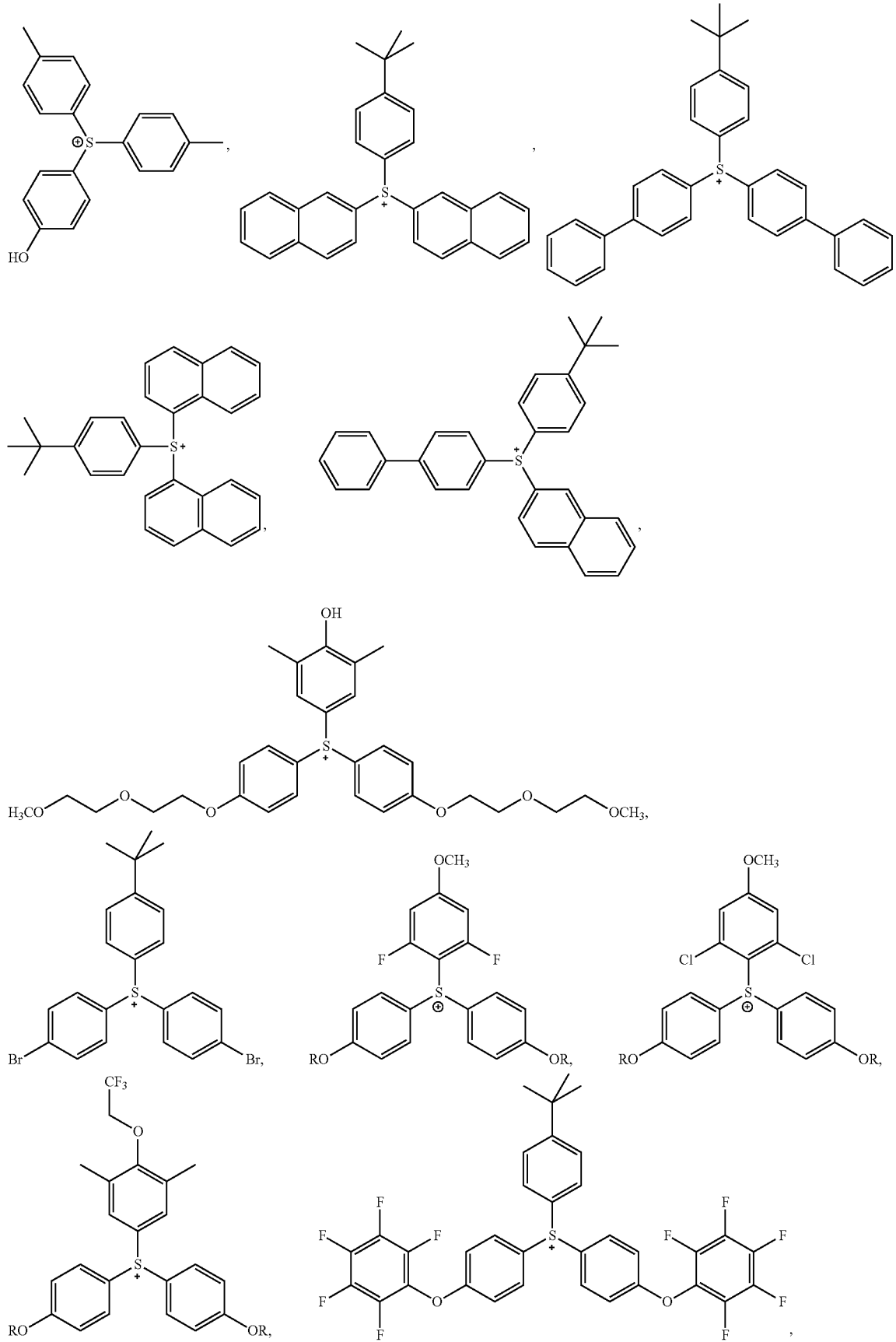

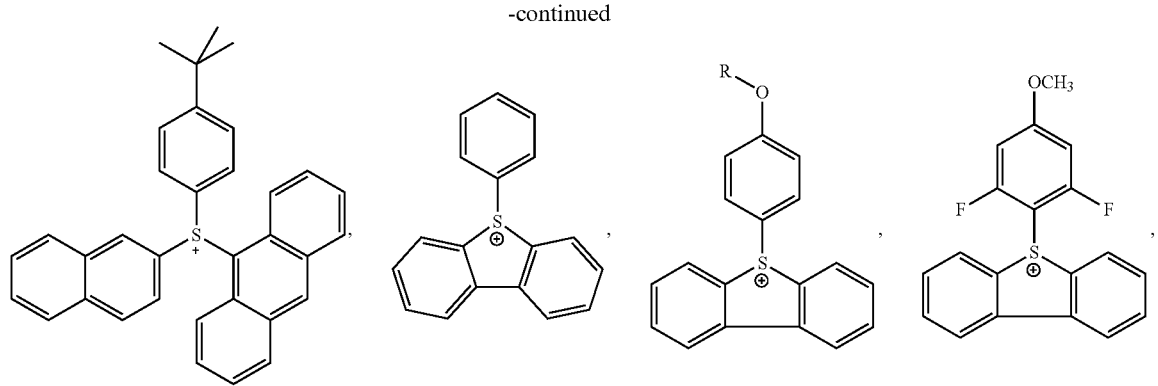
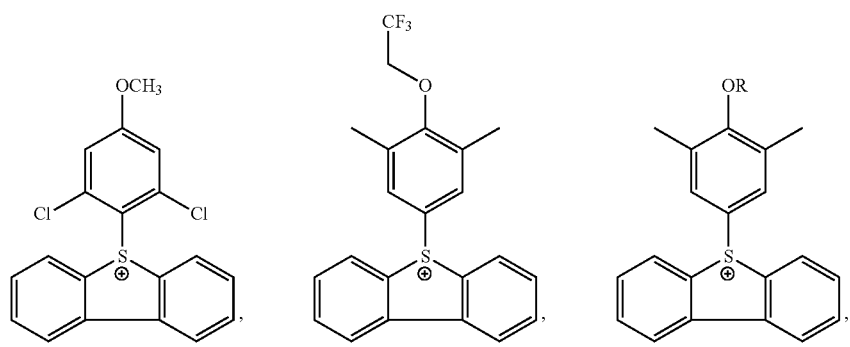
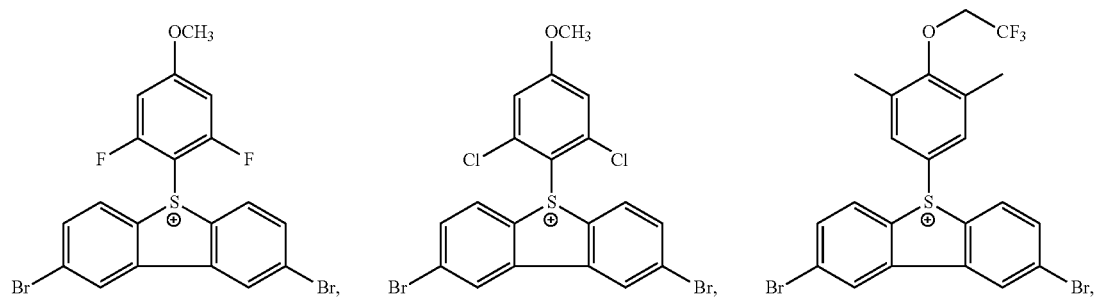
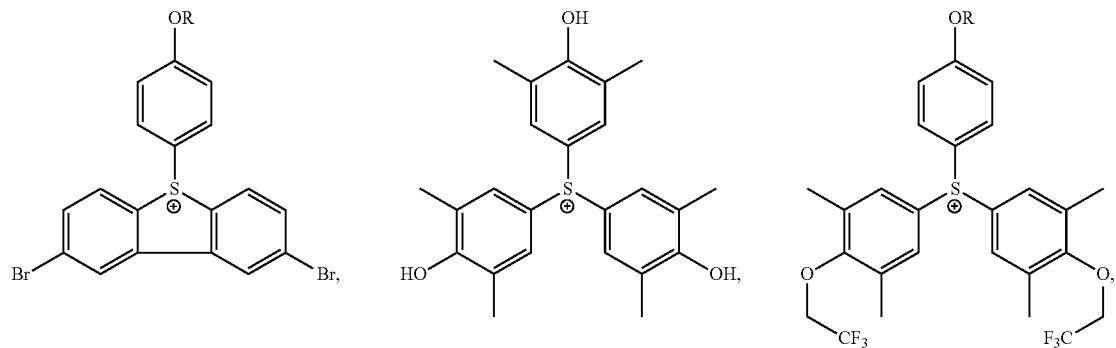

-continued
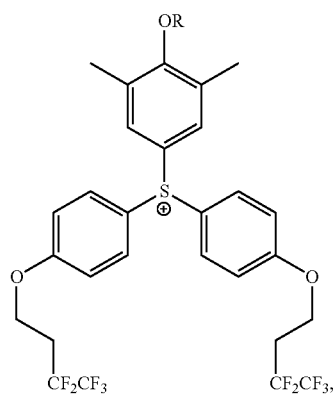
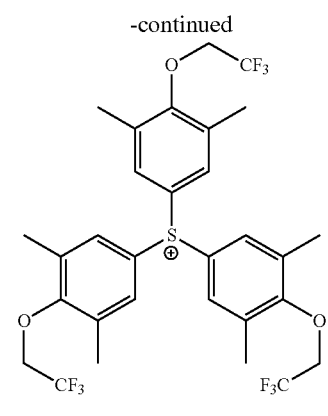
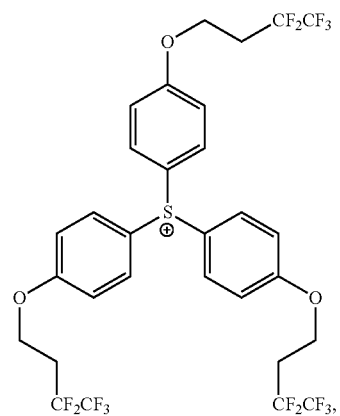
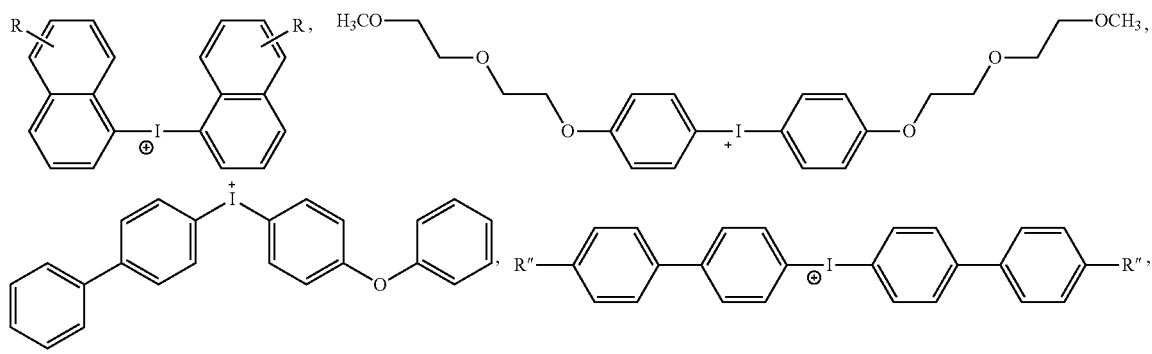
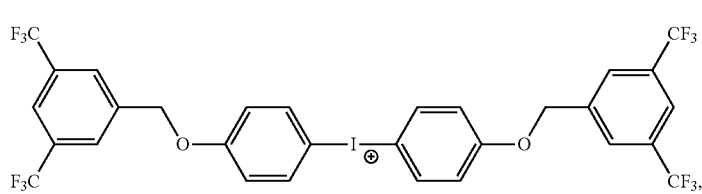
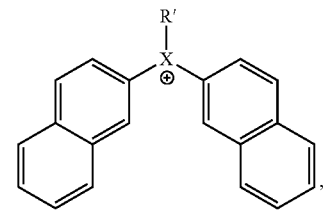
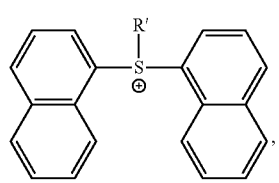
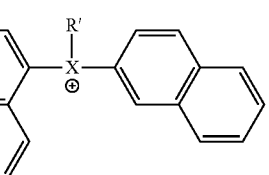
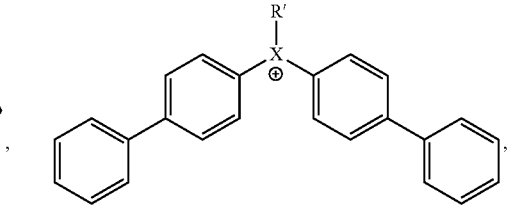
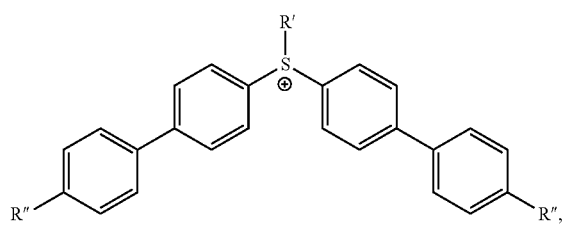
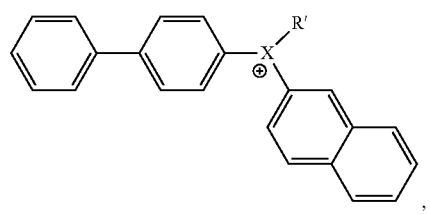
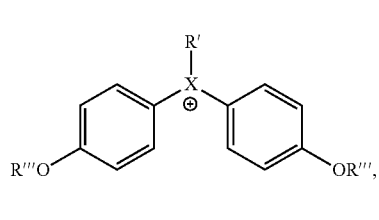
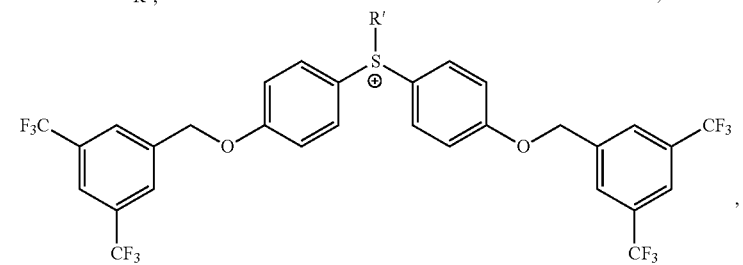

-continued
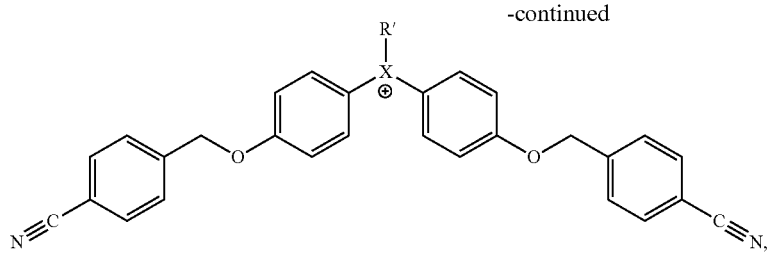
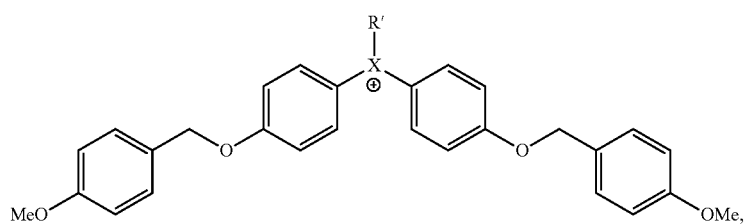
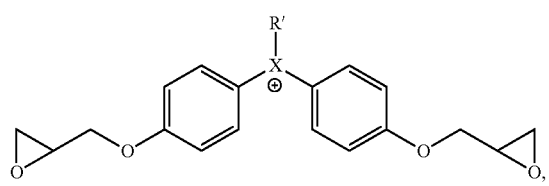
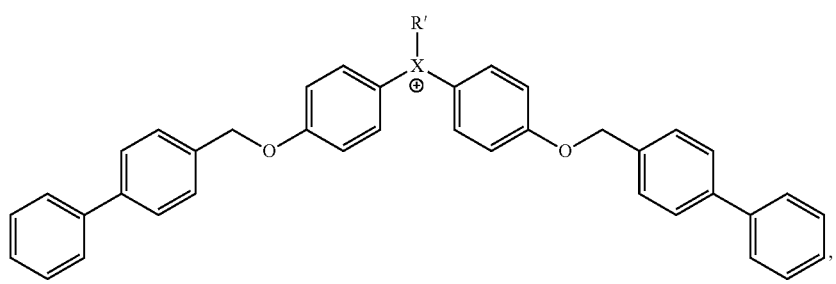
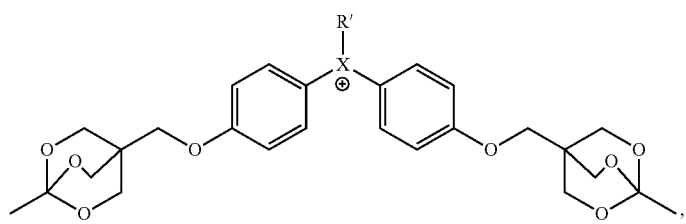
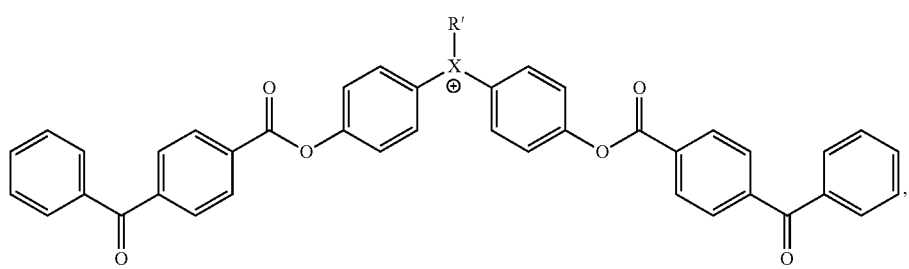
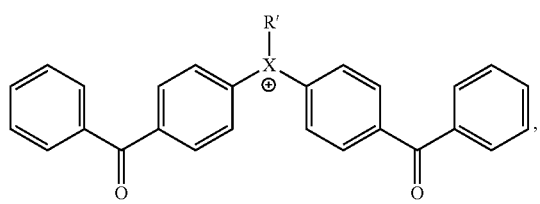

-continued
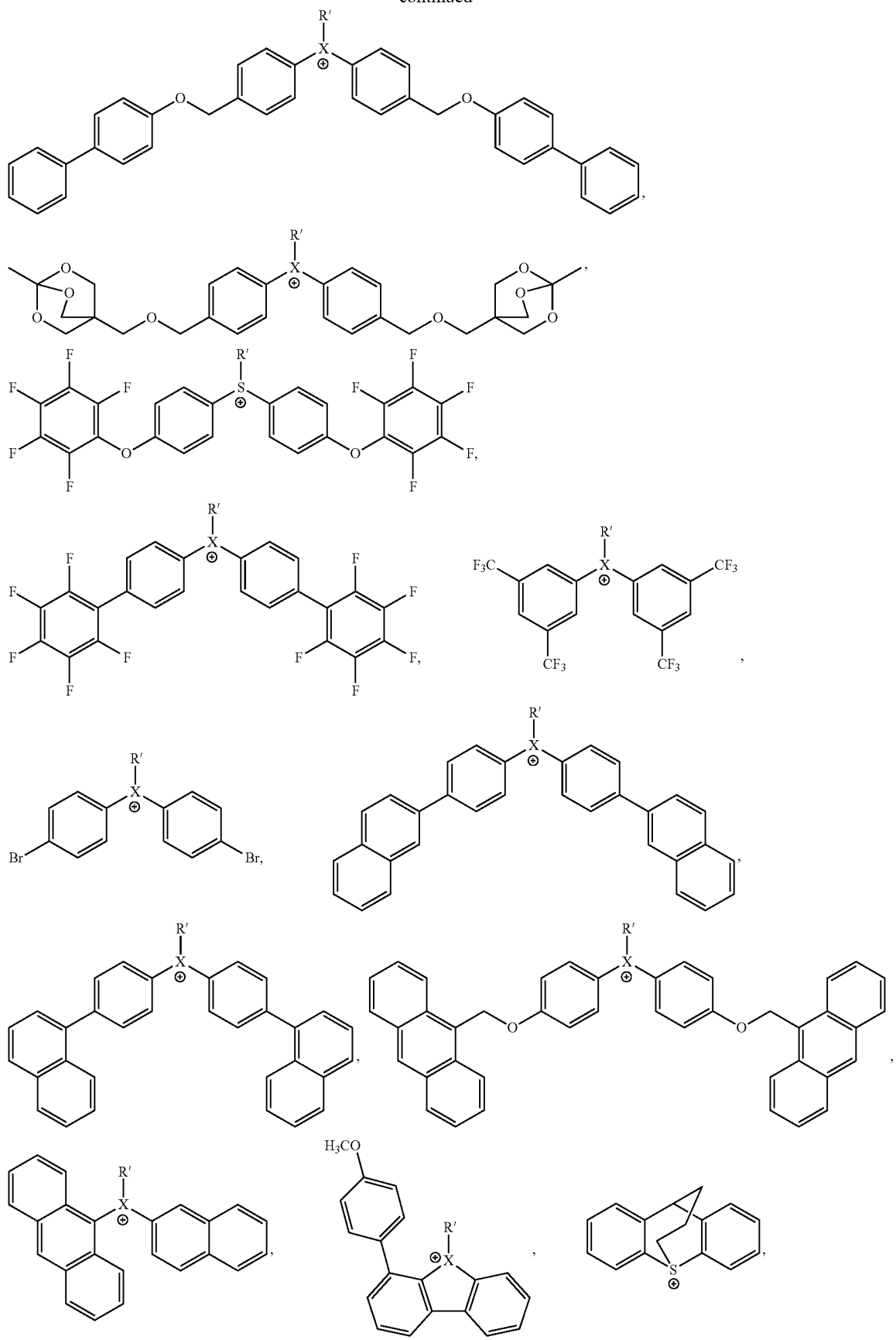

-continued

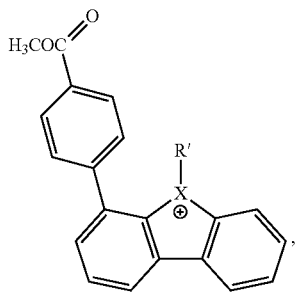 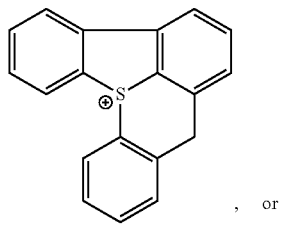, or

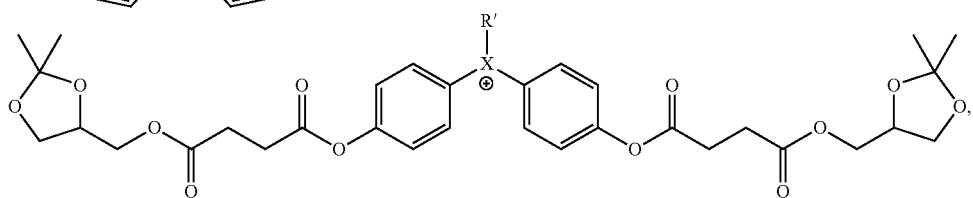

wherein X is S or I provided that where X is I, R' is a lone pair of electrons, R is $C_{1-10}$ alkyl, $C_{1-10}$ fluoroalkyl, $C_{1-10}$ alkoxy, or $C_{1-10}$ fluoroalkoxy group, where X is S, R' is a $C_{6-30}$ aryl, $C_{6-30}$ arylene, or $C_{7-20}$ alkyl-aryl group, each R" is independently H, OH, halogen, $C_{1-20}$ alkyl, $C_{1-20}$ fluoroalkyl, $C_{1-20}$ alkoxy, $C_{1-20}$ fluoroalkoxy, $C_{3-20}$ cycloalkyl, $C_{3-20}$ fluorocycloalkyl, $C_{6-20}$ aryl, $C_{7-20}$ alkyl-aryl, or a combination comprising at least one of the foregoing, and each R''' is independently H, $C_{1-20}$ alkyl, $C_{1-20}$ fluoroalkyl, $C_{1-20}$ alkoxy, $C_{1-20}$ fluoroalkoxy, $C_{3-20}$ cycloalkyl, $C_{3-20}$ fluorocycloalkyl, $C_{6-20}$ aryl, $C_{7-20}$ alkyl-aryl, or a combination comprising at least one of the foregoing.

Z in formula (I) comprises the anion of a sulfonic acid, a sulfonimide, or a sulfonamide. Preferably, Z is the anion of a $C_{1-30}$ alkanesulfonic acid, $C_{3-30}$ cycloalkanesulfonic acid, $C_{1-30}$ fluorinated alkanesulfonic acid, $C_{3-30}$ fluorinated cycloalkanesulfonic acid, $C_{6-30}$ arylsulfonic acid, $C_{6-30}$ fluorinated arylsulfonic acid, $C_{7-30}$ alkylarylsulfonic acid, $C_{7-30}$ fluorinated alkylarylsulfonic acid, $C_{1-30}$ fluorinated alkanesulfonimide, $C_{2-30}$ fluorinated cycloalkanesulfonimide, $C_{6-30}$ fluorinated arylsulfonimide, $C_{7-30}$ alkylarylsulfonimide, $C_{7-30}$ fluorinated alkylarylsulfonimide, or a combination comprising at least one of the foregoing.

Exemplary anions Z of formula (I) include those having the formulas:

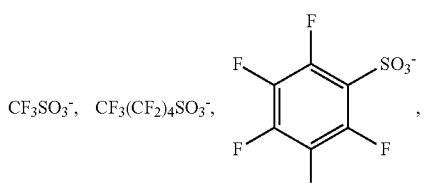

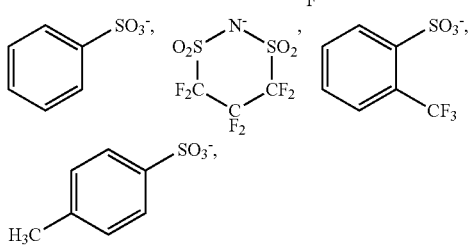

-continued

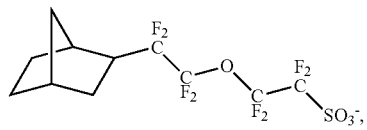

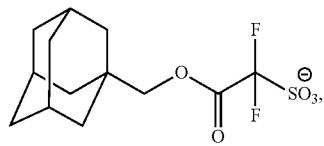

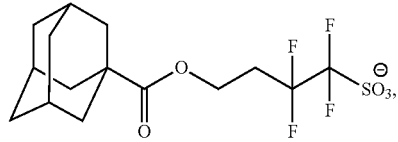

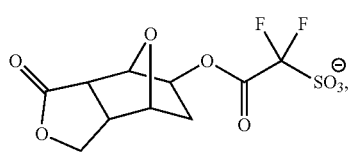

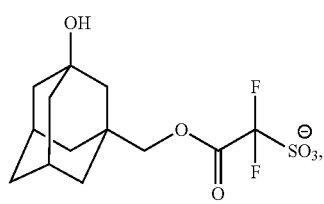

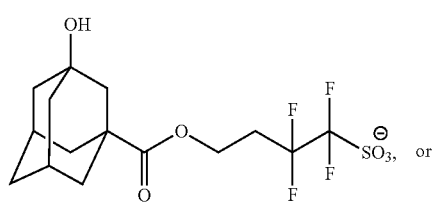, or

-continued

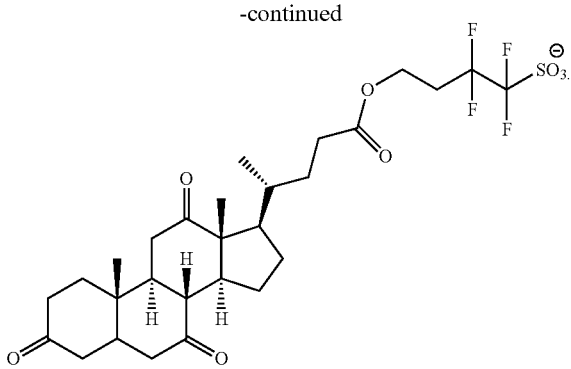

The PAGs disclosed herein are preferably useful in photoresists for EUV lithography, and may desirably have specific absorbance and decomposition characteristics when exposed to EUV radiation, over radiation of other wavelengths. For example, the EUV radiation source, in addition to an emission spectrum in the EUV region (about 12-14 nm, where the typical emission used is 13.4-13.5 nm) may emit at longer wavelengths to which photoacid generators may be sensitive, such as at 248 nm and/or 193 nm (which are also emission bands for KrF and ArF excimer lasers used in DUV and 193 nm lithographies). Sensitivity of the PAGs disclosed herein toward EUV is high, and to these other emission lines, referred to in the art as "Out-of-Band" (OOB) emission wavelengths, is preferably minimal, i.e., lower than that of PAGs typically used at such wavelengths (248 or 193 nm), such as triphenylsulfonium (TPS) PAGs or di-(t-butylphenyl) iodonium PAGs. The PAGs disclosed herein may preferably have an OOB sensitivity toward either 248 or 193 nm radiation, reported as a ratio of dose-to-clear ($E_0$, reported in mJ/cm$^2$) for a photoresist prepared using the PAG at EUV and 248 or 193 nm exposure conditions, of less than or equal to 1.5, specifically less than or equal to 1.3, more specifically less than or equal to 1.1, and still more specifically less than or equal to 1.0.

The PAGs may be prepared by a suitable general method used to prepare iodonium or sulfonium PAGs. The iodonium photoacid generators disclosed herein may generally be prepared by any of several different methods. For example, bisaryl iodonium salts may be prepared by simple condensation of $C_{6-30}$ aryl groups substituted with electron donating groups such as, for example, alkyl groups, olefinic groups, hydroxy groups, ether groups, other aromatic groups such as phenyl groups substituted with electron donating groups (e.g. phenoxy groups), and other similar groups, with an iodate salt such as potassium iodate ($KIO_3$) under strongly acidic/dehydrating conditions (e.g., sulfuric acid and acetic anhydride) to provide the bis-aryl substituted iodonium salt precursor. Other methods useful for making both symmetric and asymmetrically substituted iodonium salt precursors in higher yield include oxidation of an aryl iodide in the presence of sodium perborate ($NaBO_3$) and acetic acid, and condensation with a second aryl iodide having an electron donating group, or with Koser's Reagent (an aryl hydroxyiodoniumtosylate, i.e., Ar—I(OH)(OTs)).

Sulfonium photoacid generators may generally be prepared by, for example, combining a sulfinyl diaryl compound (i.e., a diaryl sulfoxide prepared from $C_{6-30}$ aryl groups preferably substituted with electron donating groups as described above) with another group such as a $C_{6-30}$ aryl compound or $C_{1-30}$ alkyl group, preferably one having electron donating groups, in the presence of a suitable dehydrating agent or Lewis acid (such as, for example, sulfuric acid or Eaton's reagent) for promoting condensation of the sulfinyl group with the aryl or alkyl compound, to generate the cation. It will be appreciated that the condensation of the sulfinyl diaryl compound may also be an intramolecular condensation with a substituent group.

Iodonium or sulfonium salts prepared by any of these methods may be further subject to a methathesis anion exchange using an appropriate acid or salt of an acid, imide, or amide to provide the corresponding iodonium or sulfonium salt with the desired anion (e.g., Z, as described above). Preferably, the anion used in the metathesis exchange is a sulfonic acid or salt thereof, or the salt of a sulfonamide or sulfonimide.

The PAG compounds disclosed hereinabove are useful for preparing photoresists. In an embodiment, a photoresist includes the PAG compound and a polymer comprising acid sensitive functional groups.

The polymer may be any polymer useful in a photoresist, without limitation; for example, polymers useful for preparing photoresists which may be used in chemically amplified positive or negative tone photoresists for DUV (248 nm) and 193 nm exposure are contemplated. Preferably however, the polymer is one useful for preparing photoresists for imaging with an actinic radiation for advanced microlithography, such as x-ray, e-beam, or EUV as discussed hereinabove. It will be understood that "polymer" used in this context of a component in a photoresist may mean one polymer, more than one polymer, or a combination of one or more polymers with another one or more polymers useful in a photoresist.

Preferred polymers may include in a combination of two or more polymerized units, each of which imparts a different property to the polymer. Preferably, the polymer includes a first polymerized unit comprising an acid sensitive functional group, and a second polymerized unit comprising a base-soluble functional group. The first polymerized unit may be formed from a $C_{10-30}$ acid sensitive olefinic ester monomer having an acid-sensitive functional group. The acid-sensitive group may be a cyclic alkyl group, polycyclic alkyl group, or aromatic group, having a tertiary alkyl center to which the olefinic ester is attached. The first polymerized unit may preferably be formed from a compound having the formula:

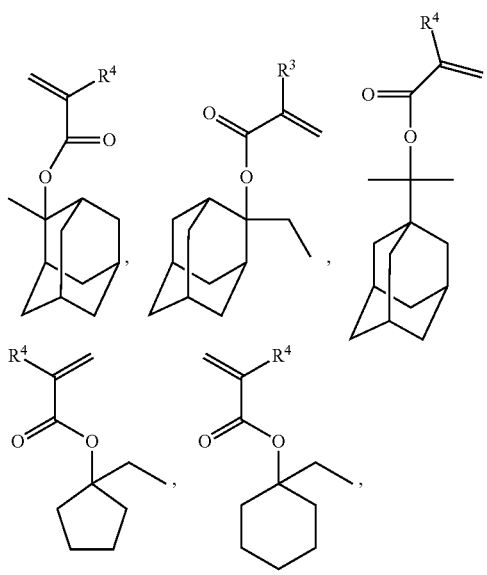

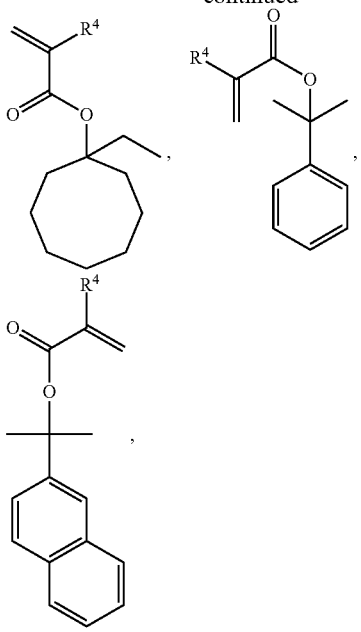

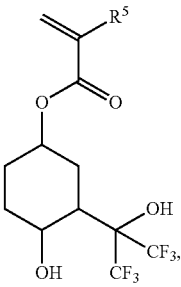

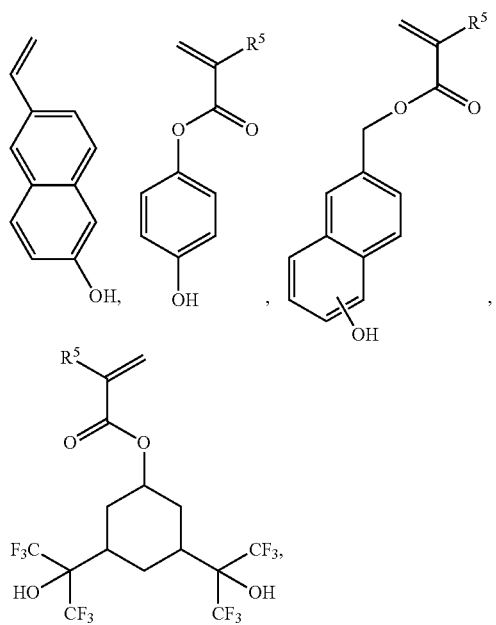

or a combination comprising at least one of the foregoing, wherein $R^4$ is H, F, $C_{1-6}$ alkyl, or $C_{1-6}$ fluoroalkyl. Preferred exemplary monomers include those in which $R^4$ in the above structures is a —$CH_3$ group (i.e., a (meth)acrylate group).

The second polymerized unit may be formed from a $C_{10-30}$ base-soluble olefinic ester monomer having an base-soluble functional group. The base-soluble functional group may be the olefinic ester of a cyclic alkyl group or polycyclic alkyl group having a hexafluoroisopropanol group and optionally a second polar group such as a hydroxy, or a vinyl aromatic or olefinic ester an aromatic group having a phenolic hydroxy group or a hexafluoroisopropanol group as the base-soluble functional group. The second polymerized unit may preferably be formed from a base-soluble monomer of the formula:

or a combination comprising at least one of the foregoing, wherein $R^5$ is H, F, $C_{1-6}$ alkyl, or $C_{1-6}$ fluoroalkyl.

It will be appreciated that all polymers containing the above-identified monomers of the first and second polymerized units are contemplated with the photoacid generators disclosed herein. It will be appreciated that additional monomeric units may further be included in the polymer, such as for example those derived from $C_{8-20}$ vinyl aromatic groups such as styrene, 4-hydroxystyrene, etc; $C_{7-20}$ cyclic olefins including norbornene and substituted norbornenes, on $C_{4-20}$ olefinic anhydrides such as maleic anhydride, itaconic anhydride, citraconic anhydride, etc.; other $C_{10-30}$ (meth)acrylate monomers including those having lactone functional groups such as, for example, alpha-(gammabutyrolactone) (meth)acrylate, and combinations including at least one of the foregoing.

The photoresist may include, in addition to the PAG compound and polymer, additives including for example a photo-decomposable base, and a surfactant. Other additives, such as dissolution rate inhibitors, sensitizers, additional PAGs, etc. may also be included. The photoresist components are dissolved in solvent for dispense and coating.

The photoresist may include a photo-decomposable base. Inclusion of base materials, preferably the carboxylate salts of photo-decomposable cations, provides a mechanism for neutralization of acid from the acid decomposable groups, and limits the diffusion of the photogenerated acid, to thereby provide improved contrast in the photoresist.

Photo-decomposable bases include photo-decomposable cations, and preferably those also useful for preparing PAGs, paired with an anion of a weak (pKa>2) acid such as, for example, a $C_{1-20}$ carboxylic acid. Exemplary such carboxylic acids include formic acid, acetic acid, propionic acid, tartaric acid, succinic acid, cyclohexylcarboxylic acid, benzoic acid, salicylic acid, and other such carboxylic acids. Exemplary photo-decomposable bases include those combining cations and anions of the following structures where the cation is triphenylsulfonium or one of the following:

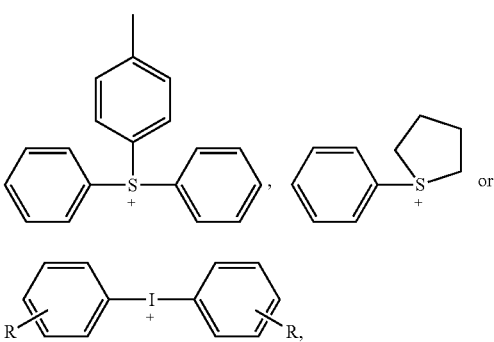

where R is independently H, a $C_{1-20}$ alkyl, a $C_{6-20}$ aryl, or a $C_{6-20}$ alkyl aryl, and the anion is

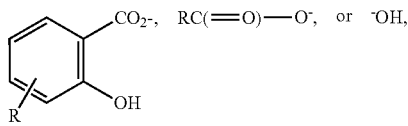

where R is independently H, a $C_{1-20}$ alkyl, a $C_{1-20}$ alkoxy, a $C_{6-20}$ aryl, or a $C_{6-20}$ alkyl aryl. Other photodecomposable bases include those based on non-ionic photodecomposing chromophores such as, for example, 2-nitrobenzyl groups and benzoin groups. An exemplary photobase generator is ortho-nitrobenzyl carbamate.

Alternatively, or in addition, other additives may include quenchers that are non-photodecomposable bases, such as, for example, those based on hydroxides, carboxylates, amines, imines, and amides. Preferably, such quenchers include $C_{1-30}$ organic amines, imines, or amides, or may be a $C_{1-30}$ quaternary ammonium salt of a strong base (e.g., a hydroxide or alkoxide) or a weak base (e.g., a carboxylate). Exemplary quenchers include amines such as Troger's base, a hindered amine such as diazabicyclo undecene (DBU) or diazabicyclononene (DBM), or ionic quenchers including quaternary alkyl ammonium salts such as tetrabutylammonium hydroxide (TBAH) or tetrabutyl ammonium lactate.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoresist further includes a solvent generally suitable for dissolving, dispensing, and coating the components used in a photoresists. Exemplary solvents include anisole, alcohols including ethyl lactate, 1-methoxy-2-propanol, and 1-ethoxy-2 propanol, esters including n-butylacetate, 1-methoxy-2-propyl acetate, methoxyethoxypropionate, ethoxyethoxypropionate, ketones including cyclohexanone and 2-heptanone, and a combination comprising at least one of the foregoing solvents.

The photoresist composition disclosed herein may include the PAG in an amount of less than or equal to 50 wt %, specifically 1 to 40 wt %, more specifically 1 to 30 wt %, and still more specifically 2 to 20 wt %, based on the total weight of solids. The photoresist composition disclosed herein also includes the polymer in an amount of 50 to 99 wt %, specifically 55 to 95 wt %, more specifically 60 to 90 wt %, and still more specifically 65 to 90 based on the total weight of solids.

The photobase generator may be present in the photoresist in an amount of 0.01 to 5 wt %, specifically 0.1 to 4 wt %, and still more specifically 0.2 to 3 wt %, based on the total weight of solids. A surfactant may be included in an amount of 0.01 to 5 wt %, specifically 0.1 to 4 wt %, and still more specifically 0.2 to 3 wt %, based on the total weight of solids. A quencher may be included in relatively small amounts of for example, from 0.03 to 5 wt % based on the total weight of solids. Other additives may be included in amounts of less than or equal to 30 wt %, specifically less than or equal to 20%, or more specifically less than or equal to 10%, based on the total weight of It will be understood that the solids includes PAG, polymer, photobase generator, quencher, surfactant, and any optional additives. The total solids content for the photoresist composition may be 0.5 to 50 wt %, specifically 1 to 45 wt %, more specifically 2 to 40 wt %, and still more specifically 5 to 35 wt %, based on the total weight of solids and solvent. It will be understood that the solids includes PAG, polymer, photobase generator, quencher, surfactant, and any optional additives, exclusive of solvent.

The photoresist including the PAGs disclosed herein may be used to provide a layer comprising the photoresist, which produces volatile degradation products in a concentration lower than that obtained for a layer comprising a comparative photoresist comprising a photoacid generator of formula (I) but in which G is a triphenylsulfonium cation, when exposed to EUV radiation under identical conditions. Relative outgassing may be determined by, for examples, residual gas analysis (RGA) or film shrinkage techniques.

A coated substrate may be formed from the photoresist containing the PAG. Such a coated substrate includes: (a) a substrate having one or more layers to be patterned on a surface thereof; and (b) a layer of the photoresist composition including the PAG over the one or more layers to be patterned.

Substrates may be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. Preferably, the surfaces of substrates herein include critical dimension layers to be patterned including, for example, one or more gate-level layers or other critical dimension layer on the substrates for semiconductor manufacture. Such substrates may preferably include silicon, SOI, strained silicon, and other such substrate materials, formed as circular wafers having dimensions such as, for example, 200 mm, 300 mm, or larger in diameter, or other dimensions useful for wafer fabrication production.

Further, a method of forming an electronic device includes (a) applying a layer of a photoresist composition including the PAG on a surface of the substrate; (b) patternwise exposing the photoresist composition layer to activating radiation; and (c) developing the exposed photoresist composition layer to provide a resist relief image.

Applying may be accomplished by any suitable method, including spin coating, spray coating, dip coating, doctor blading, or the like. Applying the layer of photoresist is preferably accomplished by spin-coating the photoresist in solvent using a coating track, in which the photoresist is dispensed on a spinning wafer. During dispense, the wafer may be spun at a speed of up to 4,000 rpm, preferably from about 500 to 3,000 rpm, and more preferably 1,000 to 2,500 rpm. The coated wafer is spun to remove solvent, and is generally baked on a hot plate to further remove residual solvent and to remove free volume from the film.

Patternwise exposure is then carried out using an exposure tool such as a stepper, in which the film is irradiated through a pattern mask and thereby is exposed pattern-wise. The method preferably uses advanced exposure tools generating activating radiation at wavelengths capable of high resolution including extreme-ultraviolet (EUV) or e-beam radiation. It will be appreciated that exposure using the activating radiation decomposes the PAG in the exposed areas and generates acid and decomposition by-products, and that the acid then effects a chemical change in the polymer (deblocking the acid sensitive group to generate a base-soluble group, or alternatively, catalyzing a cross-linking reaction in the exposed areas). The resolution of such exposure tools may be less than 30 nm.

Developing the exposed photoresist layer is then accomplished by treating the exposed layer to a suitable developer capable of selectively removing the exposed portions of the film (where the photoresist is positive tone) or removing the unexposed portions of the film (where the photoresist is negative tone). Preferably, the photoresist is positive tone based on a polymer having acid sensitive (deprotectable) groups, and the developer is preferably a metal-ion free tetraalkylammonium hydroxide solution, such as, for example, aqueous 0.26 N tetramethylammonium hydroxide. The pattern is formed after developing.

The photoresist may, when used in one or more such a pattern-forming processes, be used to fabricate electronic and optoelectronic devices such as memory devices, processor chips (CPU's), graphics chips, and other such devices.

The invention is further illustrated by the following examples. All compounds used herein are available commercially except where a procedure is provided below. Structural characterization was carried out by nuclear magnetic resonance (NMR) spectrometry on an INOVA 500 NMR Spectrometer with OMNI-PROBE (operating at 500 MHz for proton) or GEMINI 300 NMR Spectrometer (operating at 282 MHz for fluorine), each from Varian. Unless otherwise specified, all reagents were obtained commercially. The PAG of the comparative example, triphenylsulfonium 1,1,2,2,3,3,4,4,4-nonafluorobutane-1-sulfonate (TPS-PFBuS), and bis(4-tert-butylphenyl)iodonium 1,1,2,2,3,3,4,4,4-nonafluorobutane-1-sulfonate (DTBPI-PFBuS), were obtained commercially from Toyo Gosei Co. Ltd.

Example 1

Synthesis of (4-tert-butylphenyl)dinaphthalen-2-yl-sulfonium 1,1,2,2,3,3,4,4,4-nonafluorobutane-1-sulfonate. A: Synthesis of Bis(2-naphthyl)sulfide. A mixture of 2-naphthol (33.3 g, 0.23 mol), 2-naphthalenethiol (36.7 g, 0.23 mol) and p-toluenesulfonic acid (44 g, 0.23 mol) were heated to reflux in toluene (500 mL) for 4 h under $N_2$ atmosphere. After cooling, the reaction was quenched with saturated $NaHCO_3$ solution. The mixture was then extracted with $CH_2Cl_2$, the combined organic extracts were washed with $H_2O$ then concentrated to dryness by rotary evaporation. The crude product was purified by crystallization from toluene to yield 52 g (79%) of the sulfide. $^1$H NMR (CDCl$_3$) δ=7.44-7.52 (m, 3H), 7.72-7.85 (m, 3H), 7.9 (br s, 1H).

B: Synthesis of PAG. A suspension of DTBPI-PFBuS (3.4 g, 4.91 mmol), bis(2-naphthyl)sulfide (1.43 g, 4.99 mmol, 1.02 eq) as the diaryl sulfide, and copper benzoate (0.038 g, 0.124 mmol, 0.025eq) in chlorobenzene (about 10 mL) was heated to 80° C. for about 3 hours, and cooled to room temperature (herein abbreviated r.t.). The reaction mixture was concentrated by rotary evaporation under reduced pressure and the crude residue washed with boiling hexanes; drying afforded the title compound (2.94 g, 83%) as an off-white solid. $^1$H NMR (acetone-d$_6$) δ: 8.71 (s, 2H), 8.37 (d, J=9 Hz, 2H), 8.18 (d, J=8.5 Hz, 2H), 8.12 (d, J=8 Hz, 2H), 8.00 (d, J=8.5 Hz, 2H), 7.89-7.96 (m, 4H), 7.87 (t, J=8 Hz, 2H), 7.79 (t, J=8 Hz, 2H), 1.39 (s, 9H). $^{19}$F NMR (acetone-d$_6$) δ: −82.21 (3F), −115.72 (2F), 0122.38 (2F), −127.00 (2F).

Example 2

A. Synthesis of 4,4'-sulfinyldiphenol. A solution of hydrogen peroxide (30 wt % in $H_2O$, 50 mL, 0.382 mol) and triflic anhydride (32.4 mL, 0.191 mmol, 0.5 eq) in ethanol (350 mL) was added dropwise to a solution of 4,4'-thiodiphenol (125 g, 0.573 mol, 1.5 eq) in ethanol (1.25 L) over 4h. After full addition the reaction mixture was stirred at r.t. for 30 minutes, concentrated in vacuo, diluted with ethyl acetate (1 L) and washed with water (600 mL). The aqueous layer was extracted with ethyl acetate (3×600 mL), and the combined organic layers dried ($Na_2SO_4$) and concentrated in vacuo. The crude solid was diluted with methyl tert-butyl ether (1 L) and stirred overnight. The precipitate was washed with methyl tert-butyl ether (3×500 mL) and air dried to afford the title compound in quantitative yield as a white solid. $^1$H NMR (acetone-d$_6$) δ: 8.85-9.05 (brs, 2H), 7.50 (d, J=8.5 Hz, 4H), 6.95 (d, J=8.5 Hz, 4H).

B. Synthesis of (2-(2-methoxyethoxy)ethoxy)benzene. Phenol (15.0 g, 0.159 mol), potassium carbonate (26.4 g, 0.191 mol, 1.2 eq) and tetramethylethylenediamine (0.92 g, 7.95 mmol, 0.05 eq.) were dissolved in dimethylsulfoxide (DMSO; 100 mL) and stirred at r.t. for 30 minutes. 1-bromo-2-(2-methoxyethoxy)ethane (30.56 g, 0.166 mol, 1.04 eq.) was added and the solution heated to 90° C. for 18h and cooled to r.t. The reaction mixture was diluted with ethyl acetate (600 mL), washed with 1M potassium hydroxide (3×300 mL), dried ($Na_2SO_4$) and concentrated in vacuo to afford the title compound (16.50 g, 52%) as an orange oil. $^1$H NMR (acetone-d$_6$) δ: 7.27 (dt, J=8.5 Hz, 1 Hz, 2H), 6.94 (dd, J=8 Hz, 1 Hz, 2H), 6.92 (dt, J=8 Hz, 1 Hz, 1H), 4.12 (t, J=5 Hz, 2H), 3.80 (t, J=5 Hz, 2H), 3.64 (t, J=5 Hz, 2H), 3.50 (t, J=5 Hz, 2H), 3.29 (s, 3H).

C. Synthesis of 4,4'-sulfinylbis((2-(2-methoxyethoxy)ethoxy)benzene). 4,4'-sulfinyldiphenol (20.0 g, 85.0 mmol), potassium carbonate (26.6 g, 0.192 mol, 2.26 eq.) and tetramethylethylenediamine (0.495 g, 4.25 mmol, 0.05 eq.) were dissolved in DMSO (100 mL) and stirred at r.t. for 30 minutes. Then 1-bromo-2-(2-methoxyethoxy)ethane (32.67 g, 0.179 mmol, 2.1 eq.) was added, the solution heated to 90° C. for 18 h and cooled to r.t. The reaction mixture was diluted with ethyl acetate (600 mL), washed with water (5×500 mL), dried ($Na_2SO_4$) and concentrated in vacuo to afford the title compound (33.40 g, 90%) as an orange oil. $^1$H NMR (acetone-d$_6$) δ: 7.59 (d, J=8.5 Hz, 4H), 7.07 (d, J=8.5 Hz, 4H), 4.17 (t, J=4.5 Hz, 4H), 3.80 (t, J=5 Hz, 4H), 3.63 (t, J=4.5 Hz, 4H), 3.48 (t, J=4.5 Hz, 4H), 3.28 (s, 6H).

D. Synthesis of tris(4-(2-(2-methoxyethoxy)ethoxy)phenyl)sulfonium 1,1,2,2,3,3,4,4,4-nonafluorobutane-1-sulfonate. Eaton's Reagent (7.7 wt % $P_2O_5$ in methanesulfonic acid; 4 mL) was added dropwise to a solution of 4,4'-sulfinylbis((2-(2-methoxyethoxy)ethoxy)benzene) (1.00 g, 2.28 mmol), and (2-(2-methoxyethoxy)ethoxy)benzene (0.447 g, 2.28 mmol, 1 eq.) in dichloromethane (5 mL) over 2 h and stirred at r.t. overnight. The reaction mixture was slowly quenched with the addition of water (75 mL) and extracted with ethyl acetate (4×50 mL). Potassium 1,1,2,2,3,3,4,4,4-nonafluorobutane-l-sulfonate (1.54 g, 4.56 mmol, 2 eq.) was added to the aqueous layer followed by dichloromethane (100 mL) and the resulting biphasic mixture was stirred at r.t. overnight. The layers were separated and the aqueous layer extracted with dichloromethane (3×50 mL) and the combined organic layers concentrated in vacuo. The crude oil was dissolved in hot water (100 mL) and extracted with methyl tent-butyl ether (2×50 mL) followed by dichloromethane (3×100 mL). The dichloromethane layers were dried ($Na_2SO_4$) and concentrated in vacuo to afford the title compound (0.80 g, 38%) as an orange oil. $^1$H NMR (acetone-d$_6$) δ: 7.79 (d, J=9.5 Hz, 6H), 7.34 (d, J=9 Hz, 6H), 4.29 (t, J=5 Hz, 6H), 3.85 (t, J=5 Hz, 6H), 3.64 (t, J=5 Hz, 6H), 3.49 (t, J=5 Hz, 6H), 3.28 (s, 9H). $^{19}$F NMR (300 MHz, (CD$_3$)$_2$CO) δ: −82.21 (3F), −115.89 (2F), −122.42 (2F), −127.00 (2F).

Examples 3-5, 7-9

The precursor sulfides to the PAGs of Examples 3-5 and 7-9 were prepared according to the diaryl sulfide procedures below, and the corresponding PAGs were prepared according to the general procedure of Example 1 except that the specific diarylsulfide and reagent molar ratios shown in Table 1 were used, and a mixture of methyl t-butyl ether, dichloromethane, and heptane or hexane was used as the precipitation solvent.

Synthesis of bis(4-biphenyl)sulfide (precursor for Example 3). A suspension of 4-iodobiphenyl (25 g, 0.089 mol), anhydrous $Na_2S$ (3.84 g, 0.049 mol), CuI (1.7 g, 8.9 mmol) and $K_2CO_3$ (6.77 g, 0.049 mol) in anhydrous DMF (100 mL) were heated at 130° C. for 24 h under $N_2$. After cooling, water was added and the mixture was extracted with dichloromethane. The combined organic phase was washed with 2N NaOH (aq.), then water. Solvent was removed and the residue was purified by column chromatography (silica/hexanes) to yield 9.4 g (31%) of the sulfide. $^1H$ NMR ($CDCl_3$) δ 7.33-7.38 (m, 1H), 7.42-7.48 (m, 4H), 7.54-7.61 (m, 4H).

Synthesis of bis(1-naphthyl)sulfide (precursor for Example 4). A suspension of 1-iodonaphthalene (25.4 g, 0.10 mol), anhydrous $Na_2S$ (3.90 g, 0.05 mol), CuI (1.71 g, 9.0 mmol) and $K_2CO_3$ (6.91 g, 0.05 mol) in anhydrous N,N-dimethylformamide (DMF; 100 mL) were heated at 130° C. for 24 h under $N_2$. After cooling, water was added and the mixture was extracted with dichloromethane. The combined organic phase was washed with 2N NaOH, then water. Solvent was removed by rotary evaporation and the residue was purified by column chromatography (silica/hexanes) to yield 9.7 g (34%) of the sulfide. $^1H$ NMR ($CDCl_3$) δ 7.31-7.33 (m,2H), 7.51-7.56 (m,2H), 7.78 (dd, J=4.25, 4.25 Hz, 1H) 7.89 (dd, J=6.25, 3.2 Hz, 1H) 8.43 (dd, J=6.1, 3.5 Hz, 1H).

Synthesis of 4-biphenyl(2-naphthyl)sulfide (precursor for Example 5). A mixture of 2-naphthalenethiol (21.4 g, 0.134 mol), 4-iodobiphenyl (25.0 g, 0.89 mol), CuI (16.95 g, 0.089 mol), $K_2CO_3$ (12.3 g, 0.089 mol) and ethylene glycol (10 mL) in tent-amyl alcohol (500 mL) were refluxed for 48 h under $N_2$. After cooling, dichloromethane was added and the mixture was washed with 2N NaOH, water and filtered through an alumina plug. Solvent was removed under vacuum and the residue was purified by column chromatography (silica/hexanes) to yield 8.9 g (32%) of the sulfide. $^1H$ NMR ($CDCl_3$) δ 7.33-7.38 (m, 1H), 4.41-7.50 (m, 7H), 7.52-7.61 (m, 4H), 7.74-7.84 (m, 3H), 7.9 (br s, 1H).

Synthesis of (bis-4-bromophenyl)sulfide (precursor for Example 7). Bromine (38.4 g, 0.24 mol) was added dropwise at room temperature to a solution of diphenylsulfide (18.6 g, 0.1 mol) in a mixture of dichloromethane (50 mL) and $H_2O$ (50 mL). After addition, excess bromine was consumed by adding saturated aqueous sodium bisulfite. Crude product was extracted with dichloromethane, and the combined organic layers washed with water. Solvent was removed by rotary evaporation and the product was crystallized from isopropanol to yield 29.6 g (86%) of the sulfide. $^1H$ NMR ($CDCl_3$) δ 7.19 (d, J=8.5 Hz, 4H), 7.43 (d, J=8.5, 4H)

Synthesis of bis(4-pentafluorophenoxyphenyl)sulfide (precursor for Example 8). 4,4'-Thiodiphenol (20.0 g, 0.092 mol), hexafluorobenzene (68 g, 0.37 mol) and $K_2CO_3$ in anhydrous DMF (150 mL) were heated at 90° C. for 48 h under $N_2$. After cooling, water was added and the mixture extracted with dichloromethane. The organic layer was washed with water and the dichloromethane removed by rotary evaporation. The crude was purified by column chromatography (silica gel/hexanes) to yield 41 g (81.3%) of the sulfide. $^1H$ NMR ($CDCl_3$) δ 6.91 (d, J=8.75 Hz), 7.31 (d, J=8.75 Hz).

Synthesis of 9-anthracenyl(2-naphthyl)sulfide (precursor for Example 9). A mixture of 2-naphthalenethiol (15.5 g, 0.097 mol), 9-bromoanthracene (25.0 g, 0.0.097 mol), CuI (19.1 g, 0.1 mol), $K_2CO_3$ (15.0 g, 0.11 mol), KI (16.6 g, 0.1 mol) and ethylene glycol (10 mL) in tert-amyl alcohol (500 mL) were refluxed for 48 h under $N_2$. After cooling, dichloromethane was added and the mixture washed with 2N NaOH and water, and filtered through an alumina plug. Solvent was removed by rotary evaporation under vacuum and the residue purified by column chromatography (silica/hexanes) to yield 16.5 g (50.5%) of the sulfide. $^1H$ NMR ($CDCl_3$) δ 7.13 (dd, J=8.7, 1.85 Hz, 1H) 7.28-7.35 (m, 3H), 7.43-7.47 (m, 1H), 7.49-7.56 (m, 4H), 7.58 (d, J=8.7 Hz, 1H), 7.66-7.70 (m, 1H), 8.06-8.10 (m, 2H), 8.64 (s, 1H), 8.84-8.89 (m, 2H).

TABLE 1

| Example | Diarylsulfide | Amount of Diarylsulfide | DTBPI-PFBuS | copper benzoate |
|---|---|---|---|---|
| Example 3 | bis(4-biphenyl) sulfide | 1.05 eq, 2.00 g, 5.91 mmol | 1 eq, 3.90 g, 5.63 mmol | 2.5 mol %, 0.043 g, 0.141 mmol |
| Example 4 | bis(1-naphthyl) sulfide | 1.05 eq, 2.00 g, 6.98 mmol | 1 eq, 4.61 g, 6.65 mmol | 2.5 mol %, 0.051 g, 0.166 mmol |
| Example 5 | (4-biphenyl)(2-naphthyl) sulfide | 1.05 eq, 2.00 g, 6.40 mmol | 1 eq, 4.22 g, 6.10 mmol | 2.5 mol %, 0.047 g, 0.153 mmol |
| Example 7 | bis(4-bromophenyl) sulfide | 1.05 eq, 3.00 g, 8.72 mmol | 1 eq, 5.75 g, 8.30 mmol | 2.5 mol %, 0.063 g, 0.208 mmol |
| Example 8 | bis(4-(pentafluorophenyloxy)phenyl) sulfide | 1.05 eq, 3.00 g, 5.45 mmol | 1 eq, 3.59 g, 5.19 mmol | 2.5 mol %, 0.040 g, 0.130 mmol |
| Example 9 | (2-naphthyl)(9-anthracenyl)sulfide | 1.05 eq, 4.24 g, 12.6 mmol | 1 eq, 8.31 g, 12.0 mmol | 2.5 mol %, 0.092 g, 0.300 mmol |

Example 6

The PAG of Example 6 was prepared according to the procedure of Example 2, steps A. and D., except that in step D., 2,6-dimethyphenol (0.975 g, 7.98 mmol. 1 eq.), available commercially (Sigma-Aldrich) was used in place of (2-(2-methoxyethoxy)ethoxy)benzene, and 3.50 g (7.98 mmol, 1 eq.) of 4,4'-sulfinylbis((2-(2-methoxyethoxy)ethoxy)benzene) and 3.24 g (9.58 mmol, 1.2 eq,) of potassium 1,1,2,2,3,3,4,4,4-nonafluorobutane-1-sulfonate were used.

Table 2 shows characterization data ($^1H$ NMR) for the PAGs of Examples 3-9.

TABLE 2

| Example | Yield | $^1$H NMR, 500 MHz: |
|---|---|---|
| Example 3 | 55% | δ 8.10-8.17 (m, 4H), 8.03-8.09 (m, 4H), 7.91-8.00 (m, 4H), 7.76-7.83 (m, 4H), 7.47-7.59 (m, 6H), 1.40 (s, 9H) |
| Example 4 | 39% | δ 8.53 (d, J = 8 Hz, 2H), 8.43-8.47 (m, 2H), 8.28-8.33 (m, 2H), 8.01 (d, J = 8.5 Hz, 2H), 7.93 (d, J = 8.5 Hz, 2H), 7.80-7.87 (m, 6H), 7.68 (d, J = 8 Hz, 2H), 1.37 (s, 9H) |
| Example 5 | 75% | δ 8.69 (d, J = 2 Hz, 1H), 8.38 (d, J = 8.5 Hz, 1H), 8.18 (d, J = 8.5 Hz, 1H), 8.12-8.16 (m, 3H0, 8.07 (d, J = 8.5 Hz, 2H), 7.98 (d, J = 8.5 Hz, 2H), 7.85-7.94 (m, 4H), 7.78-7.82 (m, 3H), 7.48-7.58 (m, 3H), 1.39 (s, 9H) |
| Example 6 | 82% | δ 8.20-9.20 (brs, 1H), 7.78 (d, J = 9 Hz, 4H), 7.51 (s, 2H), 7.33 (d, J = 9 Hz, 4H), 4.28-4.31 (m, 4H), 3.83-3.87 (m, 4H), 3.63-3.67 (m, 4H), 3.48-3.51 (m, 4H), 3.28 (s, 6H), 2.31 (s, 6H) |
| Example 7 | 64% | δ 8.03 (d, J = 9 Hz, 4H), 7.88-7.95 (m, 8H), 1.38 (s, 9H) |
| Example 8 | 67% | δ 8.00 (d, J = 9.5 Hz, 4H), 7.85-7.91 (m, 4H), 7.59 (d, J = 9 Hz, 4H), 1.37 (s, 9H) |
| Example 9 | 38% | δ 9.48 (s, 1H), 8.69 (d, J = 8.5 Hz, 2H), 8.68 (s, 1H), 8.49 (d, J = 8.5 Hz, 2H), 8.31 (d, J = 9 Hz, 1H), 8.14 (d, J = 8 Hz, 1H), 8.04 (d, J = 9 Hz, 2H), 8.00 (d, J = 9 Hz, 1H), 7.77-7.93 (m, 8H), 7.72 (t, J = 8 Hz, 1H), 1.36 (s, 9H) |

Example 10

Synthesis of Biphenyl-4-yl(4-phenoxyphenyl)iodonium 1,1,2,2,3,3,4,4,4-nonafluorobutane-1-sulfonate. Sodium perborate tetrahydrate (55 mmol, 8.46 g) is added in portions to a solution of 4-iodobiphenyl (5.00 mmol, 1.40 g) in glacial acetic acid (45 mL) at 40° C., stirred for 8 h and cooled to room temperature. The reaction volume is decreased to 20 mL in vacuo, diluted with water (50 mL) and extracted with dichloromethane (3×20 mL). The combined organic fractions are dried (MgSO$_4$) and concentrated in vacuo to afford 4-diacetoxyiodobiphenyl, which is used in the next step without further purification.

A solution of p-toluenesulfonic acid (1 eq, 0.364 g, 2.00 mmol) in acetonitrile (3 mL) is added to a solution of 4-diacetoxyiodobiphenyl (1 eq, 0.796 g, 2.00 mmol) in acetonitrile (3 mL) followed by phenyl ether (1 eq, 0.340 g, 2.00 mmol) in acetonitrile (1 mL) and stirred at room temperature for 2 h. The reaction mixture is diluted with water (20 mL) and extracted with heptane (3×10 mL). Dichloromethane (20 mL) is added to the aqueous layer, followed by potassium 1,1,2,2,3,3,4,4,4-nonafluorobutane-1-sulfonate (1.1 eq, 0.744 g, 2.20 mmol) and stirred at room temperature overnight. The organic layer is washed with water (3×20 mL), dried (MgSO$_4$) and concentrated in vacuo to afford the title compound.

The PAG cations from Examples 1-10 are shown below in Table 3; each was prepared with 1,1,2,2,3,3,4,4,4-nonafluorobutane-1-sulfonate (perfluorobutane sulfonate, PFBuS) anion, according to the following synthetic procedures.

TABLE 3

Example 1

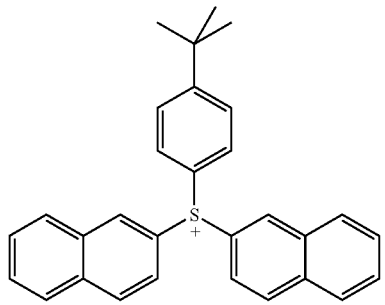

TABLE 3-continued
Example 2
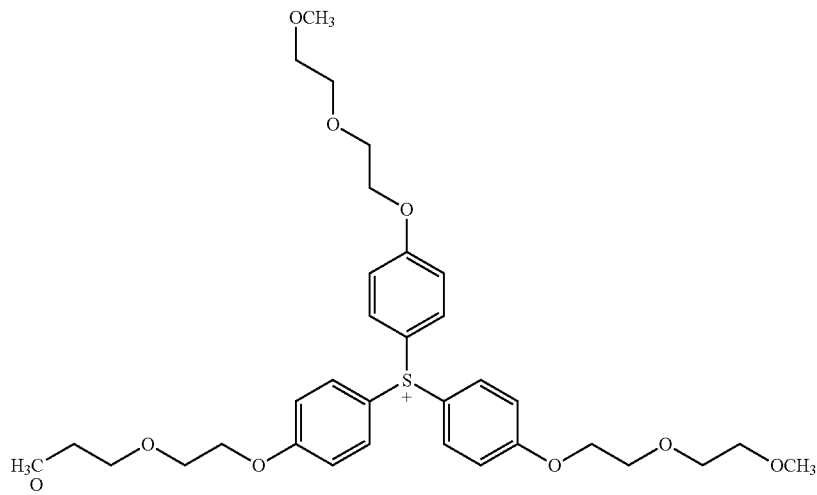
Example 3
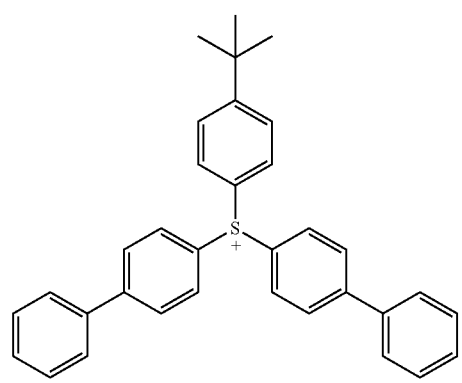
Example 4
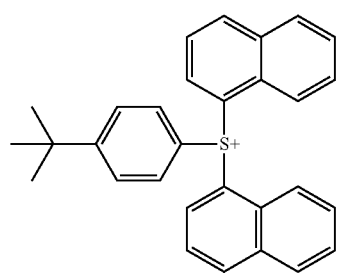 [SMILES: CC(C)(C)c1ccc([S+](c2cccc3ccccc23)c2cccc3ccccc23)cc1]
Example 5
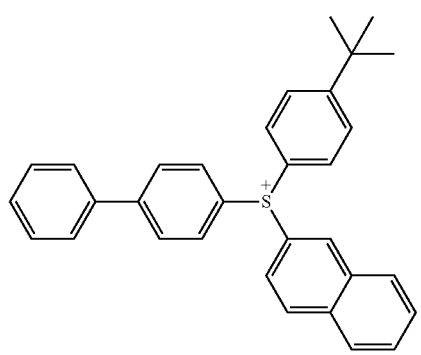

TABLE 3-continued
Example 6
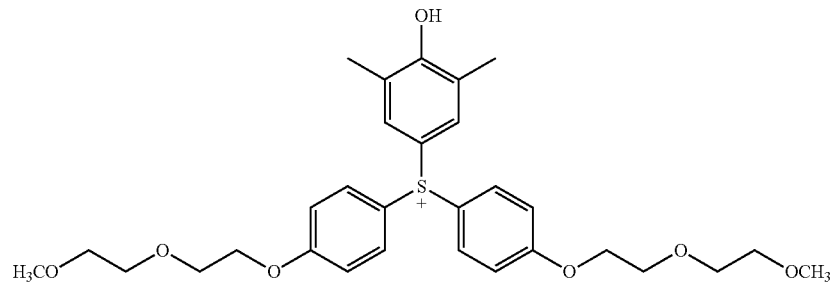
Example 7
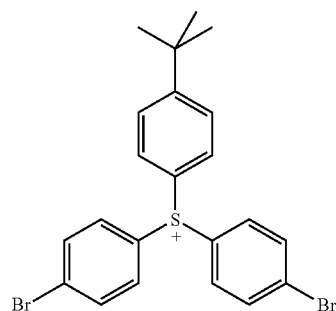
Example 8
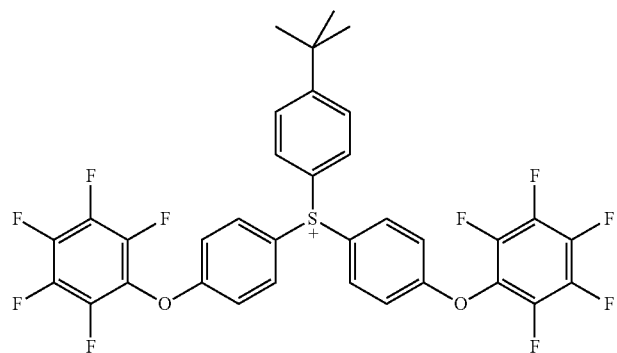
Example 9
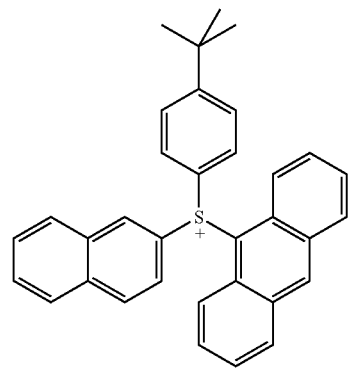

TABLE 3-continued

Example 10

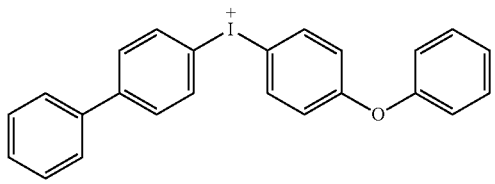

⁻PFBuS

Comp. Ex.

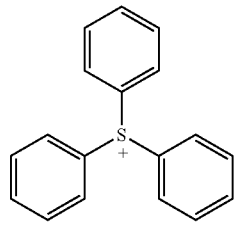

Synthesis of Polymer A. 1-Ethylcyclopentyl methacrylate (59.24 g, 0.325 mole), (2-isopropyl)-2-adamantyl methacrylate (12.18 g, 0.046 mole), alpha-(gamma-butyrolactone) methacrylate (39.51 g, 0.232 mole), (3-hydroxy)-1-adamantyl methacrylate (65.84 g, 0.279 mole), and 3,5-bis(1,1,1,3,3,3-hexafluoro-2-hydroxypropan-2-yl)cyclohexyl methacrylate (23.23 g, 0.046 mole) were dissolved in 300 g of a solvent mixture of ethyl lactate (herein, EL), propylene glycol monomethylether acetate (herein, PGMEA), and gamma-butyrolactone (40/30/30 v/v ratio, respectively). VAZO V-601 initiator (32.08 g; available from DuPont) was dissolved in 20 g of the same solvent mixture. A reactor containing an additional 280 g of the solvent mixture was heated to 70-72° C., at which temperature the initiator solution was added. After several minutes, the monomer solution was feed into the reactor over 3.5 hours. The reaction solution was held at 70° C. for an additional 30 min. The crude polymer was isolated by precipitation into 11.6 L of agitated water, collected and air-dried. The air-dried polymer was dissolved in 976.8 g of the solvent mixture and precipitated into 19.5 L of an agitated mixture of methanol and water (80/20 v/v ratio, respectively), collected and air-dried. The polymer was dried in a vacuum oven at 60° C., to yield 128.6 g (64%) of polymer A as a white powder (GPC: Mw=6,551, polydispersity=1.41).

Synthesis of Polymer B. 1-Ethylcyclopentyl methacrylate (48.78 g, 0.268 mole), (2-isopropyl)-2-adamantyl methacrylate (10.03 g, 0.038 mole), gamma-butyrolactone methacrylate (45.55 g, 0.268 mole), and 3,5-bis(1,1,1,3,3,3-hexafluoro-2-hydroxypropan-2-yl)cyclohexyl methacrylate (95.64 g, 0.191 mole) were dissolved in 300 g of a solvent mixture of EL, PGMEA, and gamma-butyrolactone (40/30/30 v/v ratio, respectively). VAZO V-601 initiator (27.29 g, available from DuPont) was dissolved in 20 g of the solvent mixture. A reactor containing an additional 280 g of the solvent mixture was heated to 70-75° C., at which temperature the initiator solution was added. After several minutes, the monomer solution was feed into the reactor over 3.5 hours. The reaction solution was held at 70-71° C. for an additional 30 min. The crude polymer was isolated by precipitation into 12 L of an agitated mixture of methanol and water (50/50 v/v ratio, respectively), collected, and air-dried. The air-dried polymer was dissolved in 760.2 g of the solvent mixture, precipitated into 15.2 L of an agitated mixture of methanol and water (50/50 v/v ratio, respectively), collected, and air-dried. The polymer was vacuum oven dried at 60° C., to yield 165 g (82%) of Polymer B as a white powder (GPC: Mw=6,655, polydispersity=1.60).

Photoresist preparation and processing. Comparative Formulation Example. A positive-tone photoresist composition was prepared by combining 5.563 g of a 10 wt % solution in EL of Polymer A, 5.563 g of a 10 wt % solution in EL of the Polymer B, 6.250 g of a 2 wt % solution in EL of TPS-PFBuS (Comparative PAG Example), 1.113 g of a 1 wt % solution of Troger's Base in PGMEA, 0.250 g of 0.5 wt % a solution of Omnova PF656 surfactant in EL, 21.51 g of EL solvent and 9.750 g g of PGMEA. The formulated resist was filtered (0.2 μm).

Formulation Examples 1-8

Positive-tone photoresist compositions containing PAGs of Examples 1-6, 8, and 9 were prepared according to the formulation described for the Comparative Formulation Example (CFEx), substituting the amounts specified in Table 4.

TABLE 4

| Formulation Example | Polymer A (10 wt % in EL) | Polymer B (10 wt % in EL) | PAG | Amt. PAG (2 wt % in EL) | Troger's Base (1 wt % in PGMEA) | Omnova PF 656 (0.5 wt % in EL) | EL | PGMEA |
|---|---|---|---|---|---|---|---|---|
| 1 | 5.390 g | 5.389 g | Ex. 1 | 7.988 g | 1.113 g | 0.250 g | 20.12 g | 9.750 g |
| 2 | 5.169 g | 5.170 g | Ex. 2 | 10.188 g | 1.113 g | 0.250 g | 18.36 g | 9.750 g |
| 3 | 5.330 g | 5.330 g | Ex. 3 | 8.581 g | 1.113 g | 0.250 g | 19.65 g | 9.750 g |

TABLE 4-continued

| Formulation Example | Polymer A (10 wt % in EL) | Polymer B (10 wt % in EL) | PAG | Amt. PAG (2 wt % in EL) | Troger's Base (1 wt % in PGMEA) | Omnova PF 656 (0.5 wt % in EL) | EL | PGMEA |
|---|---|---|---|---|---|---|---|---|
| 4 | 5.390 g | 5.389 g | Ex. 4 | 7.988 g | 1.113 g | 0.250 g | 20.12 g | 9.750 g |
| 5 | 5.359 g | 5.359 g | Ex. 5 | 8.294 g | 1.113 g | 0.250 g | 19.88 g | 9.750 g |
| 6 | 5.252 g | 5.252 g | Ex. 6 | 9.363 g | 1.113 g | 0.250 g | 19.02 g | 9.750 g |
| 7 | 3.057 g | 3.057 g | Ex. 8 | 13.110 g | 0.668 g | 0.150 g | 4.11 g | 5.850 g |
| 8 | 3.201 g | 3.201 g | Ex. 9 | 10.245 g | 0.668 g | 0.150 g | 6.69 g | 5.850 g |

The above photoresist formulations CFEx and Formulation Examples (FEx) 1-8 were lithographically processed as follows. The formulated resist was spin coated using TEL ACT-8 (Tokyo Electron) coating track onto a 200 mm silicon wafer having a bottom antireflective coating (BARC) thereon (for 248 nm exposure AR™9, Rohm and Haas Electronic Materials LLC or for 193 nm exposure AR™19, Rohm and Haas Electronic Materials LLC, or an organic underlayer for EUV), and soft baked at 130° C. for 90 seconds, to form a resist film of about 60 nm in thickness. The photoresist layer was exposed through a photomask with 248 nm KrF excimer laser radiation, 193 nm ArF excimer laser radiation, or EUV radiation (eMET, 13.4-13.5 nm) radiation and the exposed layers were post-exposed baked (PEB) at 90° C. for 60 seconds. The coated wafers were next treated with a metal ion free base developer (0.26N aqueous tetramethylammonium hydroxide solution) to develop the photoresist layer.

The dose-to-clear ($E_0$) values for each exposure wavelength and the resist clearing dose relative to EUV (out-of-band sensitivity, OOB) at 248 nm and 193 nm are shown in Table 5.

TABLE 5

| Formulation Example (Photoresist) | PAG | 248 nm $E_0$ mJ/cm$^2$ | 193 nm $E_0$ mJ/cm$^2$ | EUV $E_0$ mJ/cm$^2$ | OOB at 248 nm (EUV $E_0$/248 $E_0$) | OOB at 193 nm (EUV $E_0$/193 $E_0$) |
|---|---|---|---|---|---|---|
| CFEx. | CEx. | 4.8 | 1.4 | 2.7 | 0.6 | 1.9 |
| FEx. 1 | Ex. 1 | 8.6 | 20.0 | 3.7 | 0.4 | 0.4 |
| FEx. 2 | Ex. 2 | 2.2 | 1.3 | 2.0 | 0.9 | 1.5 |
| FEx. 3 | Ex. 3 | 20.0 | 7.3 | 5.1 | 0.3 | 0.7 |
| FEx. 4 | Ex. 4 | 20.0 | 20.0 | 5.1 | 0.3 | 0.3 |
| FEx. 5 | Ex. 5 | 13.0 | 20.0 | 3.6 | 0.3 | 0.2 |
| FEx. 6 | Ex. 6 | 3.6 | 1.8 | 1.6 | 0.4 | 0.9 |
| FEx. 7 | Ex. 8 | 8.4 | 5.0 | 3.4 | 0.4 | 0.7 |
| FEx. 8 | Ex. 9 | >22 | >7.5 | 4.4 | <0.2 | <0.6 |

As seen in Table 5, PAG Examples 1-6, 8, and 9 each show desirable sensitivity to EUV radiation as measured by $E_0$, though the Comparative Example (CFEx., having a triphenylsulfonium cation) has higher sensitivity (2.7 mJ/cm$^2$) than all but Examples 2 (at 2.0 mJ/cm$^2$) and 6 (at 1.6 mJ/cm$^2$). However, the PAGs of Examples 1, 3-6, 8 and 9 each show improved Out-of-Band sensitivity at 248 nm (OOB at 248 nm of 0.4 or less) than CFEx (OOB at 248 nm=0.6), and all PAGs of Examples 1-6, 8, and 9 show improved OOB at 193 nm (OOB at 193 nm of 1.5 or less) than CFEx (OOB at 193=1.9). Hence, it can be seen that the exemplary PAGs of Examples 1-6, 8, and 9 are both sensitive to EUV exposure and exhibit less sensitivity to non-EUV exposure wavelengths than the Comparative Example.

All ranges disclosed herein are inclusive of the endpoints, and the endpoints are independently combinable with each other. The suffix "(s)" as used herein is intended to include both the singular and the plural of the term that it modifies, thereby including at least one of that term. "Optional" or "optionally" means that the subsequently described event or circumstance can or cannot occur, and that the description includes instances where the event occurs and instances where it does not. As used herein, "combination" is inclusive of blends, mixtures, alloys, or reaction products. All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another.

The invention claimed is:

1. A compound having the formula (I):

wherein G$^+$ has the formula (II):

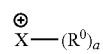

wherein in formula (II), X is S or I, each R$^0$ is commonly attached to X and is independently a C$_{1-30}$ alkyl group, a polycyclic or monocyclic C$_{3-30}$ cycloalkyl group, a polycyclic or monocyclic C$_{6-30}$ aryl group or a combination comprising at least one of the foregoing, provided that at least two occurrences of R$^0$ are polycyclic aryl groups that are different from each other and at most one occurrence of R$^0$ is naphthyl; a is 2 or 3, wherein when X is I, a is 2, or when X is S, a is 3, and Z in formula (I) comprises the anion of a sulfonic acid, a sulfonimide, or a sulfonamide.

2. The compound of claim 1, wherein G$^+$ is of the formula (V):

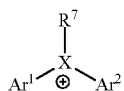
(V)

wherein X is I or S, wherein when X is I, p is 2, and when X is S, p is 3; Ar$^1$ and Ar$^2$ are different C$_{10\text{-}30}$ fused or singly bonded polycyclic aryl groups; R$^7$ is a lone pair of electrons when X is I, or a C$_{6\text{-}20}$ aryl group when X is S.

3. The compound of claim 1, wherein G$^+$ is:

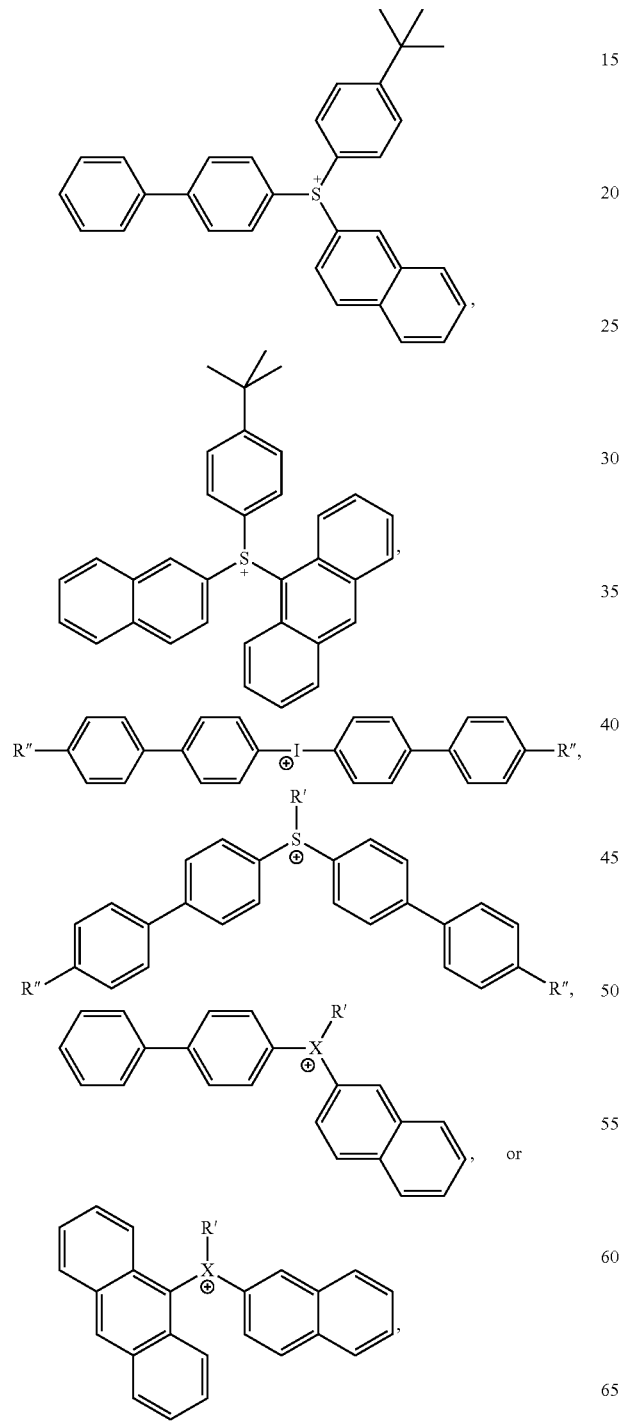

wherein X is S or I, R' is a lone pair of electrons when X is I, or C$_{6\text{-}30}$ aryl, C$_{6\text{-}30}$ arylene, or C$_{7\text{-}20}$ alkyl-aryl group when X is S, and each R" in the same molecule is different and selected from H, OH, halogen, C$_{1\text{-}20}$ alkyl, C$_{1\text{-}20}$ fluoroalkyl, C$_{1\text{-}20}$ alkoxy, C$_{1\text{-}20}$ fluoroalkoxy, C$_{3\text{-}20}$ cycloalkyl, C$_{3\text{-}20}$ fluorocycloalkyl, C$_{6\text{-}20}$ aryl, C$_{7\text{-}20}$ alkyl-aryl, or a combination comprising at least one of the foregoing.

4. The compound of claim 3, wherein Z$^-$ is the anion of a C$_{1\text{-}30}$ alkanesulfonic acid, C$_{3\text{-}30}$ cycloalkanesulfonic acid, C$_{1\text{-}30}$ fluorinated alkanesulfonic acid, C$_{3\text{-}30}$ fluorinated cycloalkanesulfonic acid, C$_{6\text{-}30}$ arylsulfonic acid, C$_{6\text{-}30}$ fluorinated arylsulfonic acid, C$_{7\text{-}30}$ alkylarylsulfonic acid, C$_{7\text{-}30}$ fluorinated alkylarylsulfonic acid, C$_{1\text{-}30}$ fluorinated alkanesulfonimide, C$_{2\text{-}30}$ fluorinated cycloalkanesulfonimide, C$_{6\text{-}30}$ fluorinated arylsulfonimide, C$_{7\text{-}30}$ alkylarylsulfonimide, C$_{7\text{-}30}$ fluorinated alkylarylsulfonimide, or a combination comprising at least one of the foregoing.

5. The compound of claim 4, wherein Z$^-$ is:

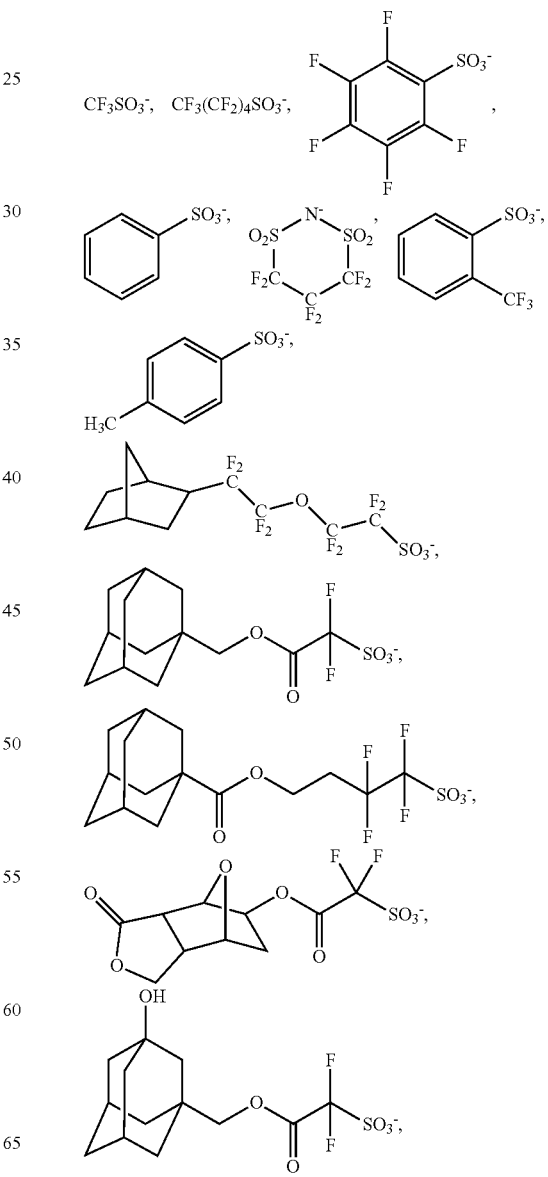

-continued

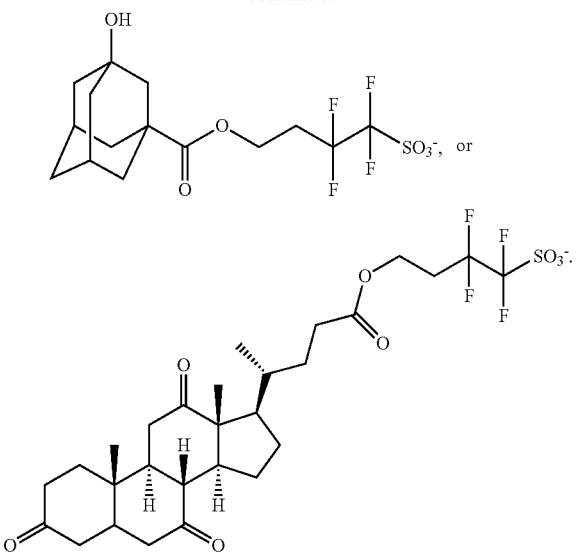

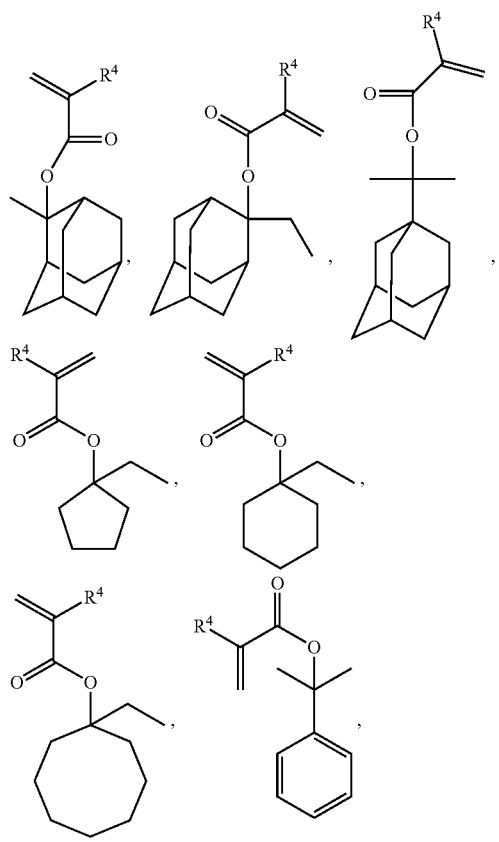

6. A photoresist comprising the compound of claim 1 and a polymer comprising acid sensitive functional groups.

7. The photoresist of claim 6, wherein polymer comprises a first polymerized unit comprising an acid sensitive functional group, and a second polymerized unit comprising a base-soluble functional group.

8. The photoresist of claim 7, wherein the first polymerized unit is formed from compounds having the formula:

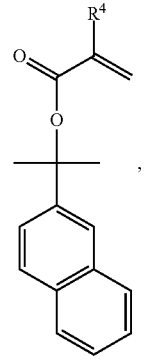

-continued

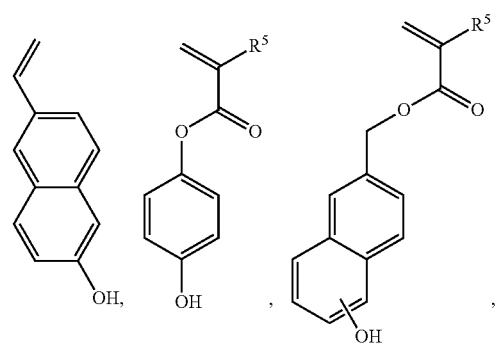

or a combination comprising at least one of the foregoing, wherein $R^4$ is H, F, $C_{1-6}$ alkyl, or $C_{1-6}$ fluoroalkyl, and the second polymerized unit is formed from a base-soluble monomer of the formula:

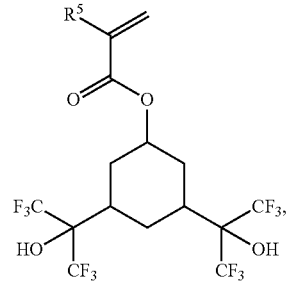

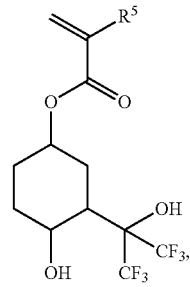

or a combination comprising at least one of the foregoing, wherein $R^5$ is H, F, $C_{1-6}$ alkyl, or $C_{1-6}$ fluoroalkyl.

9. A coated substrate, comprising:
(a) a substrate having one or more layers to be patterned on a surface thereof; and
(b) a layer of the photoresist of claim 6 over the one or more layers to be patterned.

10. A method of forming an electronic device, comprising:
(a) applying a layer of the photoresist of claim 6 on a surface of a substrate;

(b) patternwise exposing the photoresist composition layer to activating radiation; and (c) developing the exposed photoresist composition layer to provide a resist relief image.

11. The photoresist of claim 6, wherein G⁺ is of the formula (V):

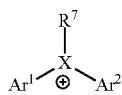

wherein X is I or S, wherein when X is I, p is 2, and when X is S, p is 3; $Ar^1$ and $Ar^2$ are different $C_{10-30}$ fused or singly bonded polycyclic aryl groups; $R^7$ is a lone pair of electrons when X is I, or a $C_{6-20}$ aryl group when X is S.

12. The photoresist of claim 6, wherein G⁺ is:

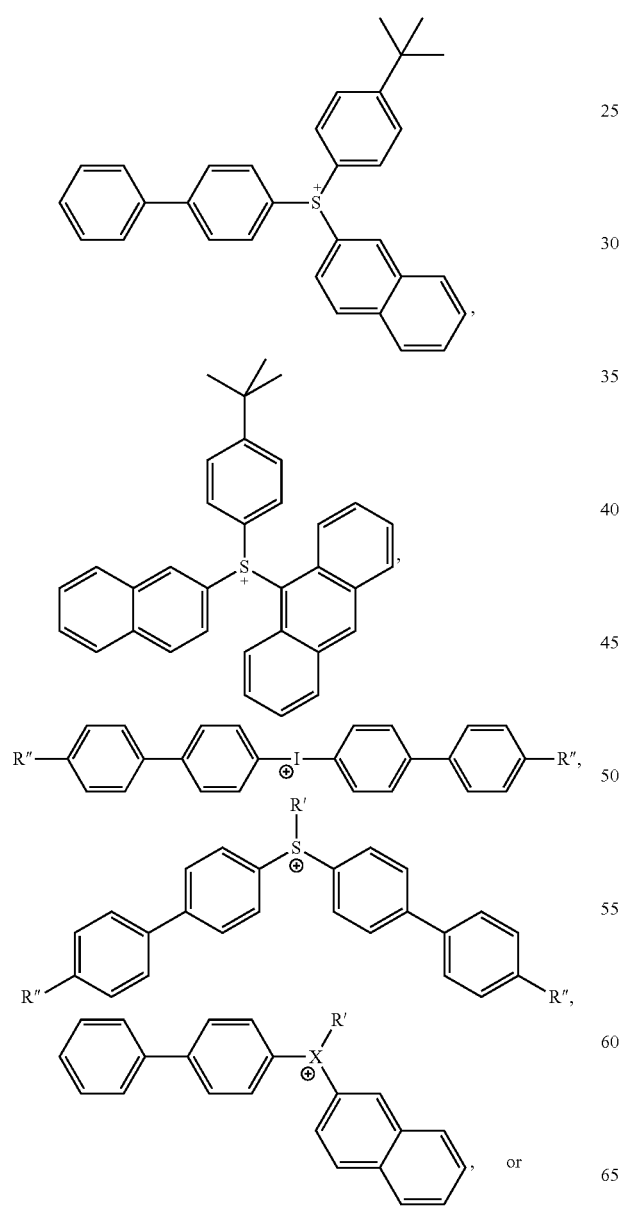

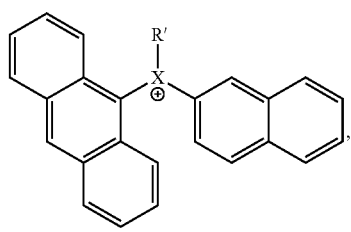

wherein X is S or I, R' is a lone pair of electrons when X is I, or $C_{6-30}$ aryl, $C_{6-30}$ arylene, or $C_{7-20}$ alkyl-aryl group when X is S, and each R" in the same molecule is different and selected from H, OH, halogen, $C_{1-20}$ alkyl, $C_{1-20}$ fluoroalkyl, $C_{1-20}$ alkoxy, $C_{1-20}$ fluoroalkoxy, $C_{3-20}$ cycloalkyl, $C_{3-20}$ fluorocycloalkyl, $C_{6-20}$ aryl, $C_{7-20}$ alkyl-aryl, or a combination comprising at least one of the foregoing.

13. The photoresist of claim 12, wherein Z⁻ is the anion of a $C_{1-30}$ alkanesulfonic acid, $C_{3-30}$ cycloalkanesulfonic acid, $C_{1-30}$ fluorinated alkanesulfonic acid, $C_{3-30}$ fluorinated cycloalkanesulfonic acid, $C_{6-30}$ arylsulfonic acid, $C_{6-30}$ fluorinated arylsulfonic acid, $C_{7-30}$ alkylarylsulfonic acid, $C_{7-30}$ fluorinated alkylarylsulfonic acid, $C_{1-30}$ fluorinated alkanesulfonimide, $C_{2-30}$ fluorinated cycloalkanesulfonimide, $C_{6-30}$ fluorinated arylsulfonimide, $C_{7-30}$ alkylarylsulfonimide, $C_{7-30}$ fluorinated alkylarylsulfonimide, or a combination comprising at least one of the foregoing.

14. The photoresist of claim 13, wherein Z⁻ is:

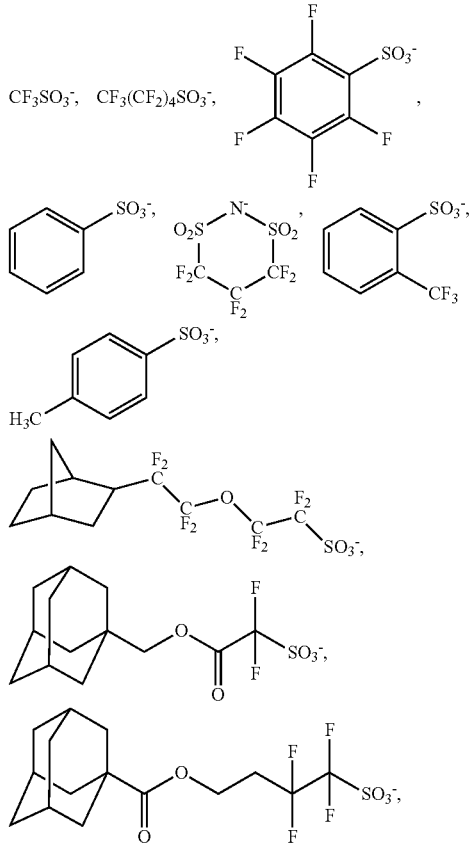

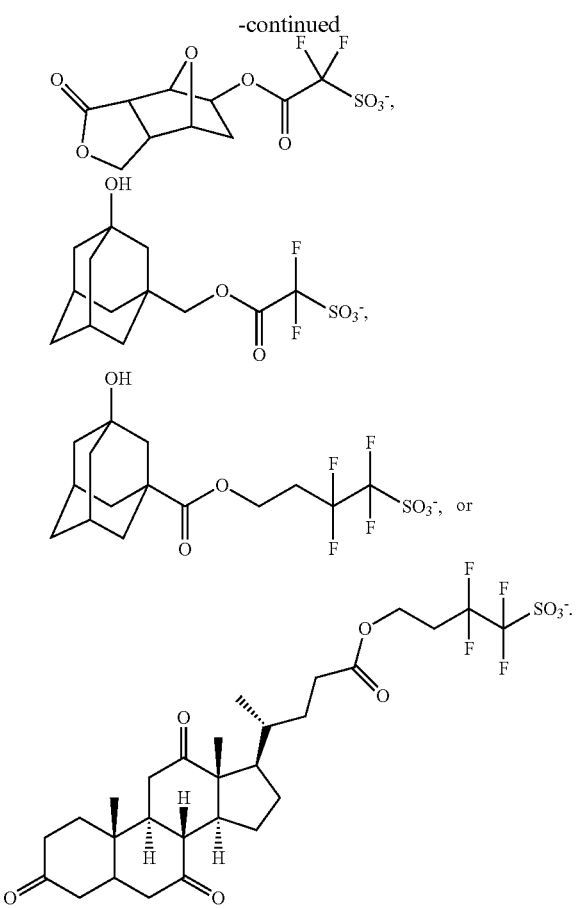

15. The method of claim 10, wherein G$^+$ is of the formula (V):

$$Ar^1 - \overset{R^7}{\underset{\oplus}{X}} - Ar^2 \quad (V)$$

wherein X is I or S, wherein when X is I, p is 2, and when X is S, p is 3; Ar$^1$ and Ar$^2$ are different C$_{10\text{-}30}$ fused or singly bonded polycyclic aryl groups; R$^7$ is a lone pair of electrons when X is I, or a C$_{6\text{-}20}$ aryl group when X is S.

16. The method of claim 10, wherein G$^+$ is:

wherein X is S or I, R' is a lone pair of electrons when X is I, or C$_{6\text{-}30}$ aryl, C$_{6\text{-}30}$ arylene, or C$_{7\text{-}20}$ alkyl-aryl group when X is S, and each R" in the same molecule is different and selected from H, OH, halogen, C$_{1\text{-}20}$ alkyl, C$_{1\text{-}20}$ fluoroalkyl, C$_{1\text{-}20}$ alkoxy, C$_{1\text{-}20}$ fluoroalkoxy, C$_{3\text{-}20}$ cycloalkyl, C$_{3\text{-}20}$ fluorocycloalkyl, C$_{6\text{-}20}$ aryl, C$_{7\text{-}20}$ alkyl-aryl, or a combination comprising at least one of the foregoing.

17. The method of claim 16, wherein Z$^-$ is the anion of a C$_{1\text{-}30}$ alkanesulfonic acid, C$_{3\text{-}30}$ cycloalkanesulfonic acid, C$_{1\text{-}30}$ fluorinated alkanesulfonic acid, C$_{3\text{-}30}$ fluorinated cycloalkanesulfonic acid, C$_{6\text{-}30}$ arylsulfonic acid, C$_{6\text{-}30}$ fluorinated arylsulfonic acid, C$_{7\text{-}30}$ alkylarylsulfonic acid, C$_{7\text{-}30}$ fluorinated alkylarylsulfonic acid, C$_{1\text{-}30}$ fluorinated alkanesulfonimide, C$_{2\text{-}30}$ fluorinated cycloalkanesulfonimide, C$_{6\text{-}30}$ fluorinated arylsulfonimide, C$_{7\text{-}30}$ alkylarylsulfonimide, C$_{7\text{-}30}$ fluorinated alkylarylsulfonimide, or a combination comprising at least one of the foregoing.

18. The method of claim 17, wherein $Z^-$ is:
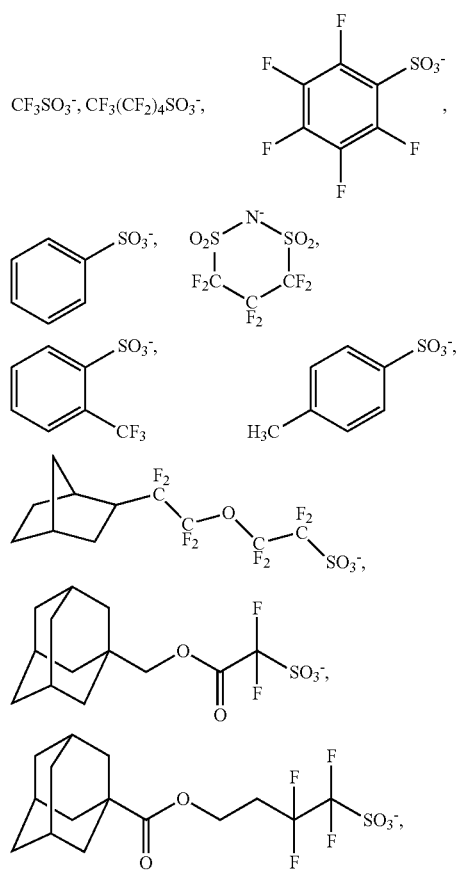
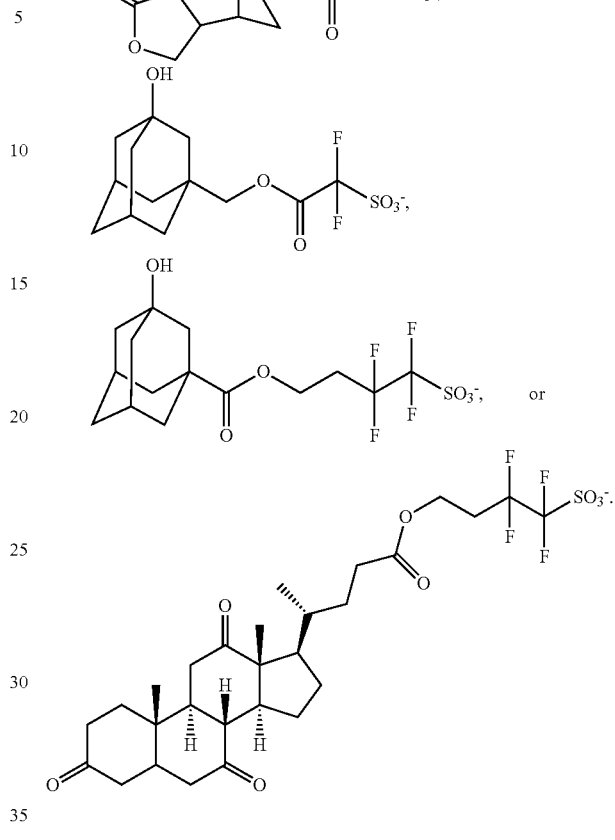
* * * * *